(12) United States Patent
Verna et al.

(10) Patent No.: US 7,370,574 B2
(45) Date of Patent: May 13, 2008

(54) DEVICE FOR DETERMINING AND MAINTAINING MOLD GYRATION ANGLE IN A GYRATORY COMPACTOR

(75) Inventors: Raffaello Verna, Creedmoor, NC (US); Dirk Matthew Steckmann, Cary, NC (US); William A. Gowan, Raleigh, NC (US); Rayvonn Donnell Core, Mebane, NC (US); William Matthew Moscrip, Durham, NC (US)

(73) Assignee: Troxler Electronic Laboratories, Inc., Research Triangle Park, NC (US)

( * ) Notice: Subject to any disclaimer, the term of this patent is extended or adjusted under 35 U.S.C. 154(b) by 37 days.

(21) Appl. No.: 11/536,124

(22) Filed: Sep. 28, 2006

(65) Prior Publication Data

US 2007/0017299 A1    Jan. 25, 2007

Related U.S. Application Data

(62) Division of application No. 10/755,123, filed on Jan. 9, 2004, now Pat. No. 7,121,149.

(60) Provisional application No. 60/439,250, filed on Jan. 10, 2003.

(51) Int. Cl.
*G01N 3/62* (2006.01)
*G01N 3/08* (2006.01)
*B30B 15/14* (2006.01)

(52) U.S. Cl. .................. 100/48; 73/1.14; 73/1.15; 73/824; 100/99

(58) Field of Classification Search .... 73/54.29–54.35, 73/1.08, 1.11, 1.75, 813, 818, 824–825, 843, 73/866, 865.9, 1.14–1.15; 100/48, 99
See application file for complete search history.

(56) References Cited

U.S. PATENT DOCUMENTS

| | | | |
|---|---|---|---|
| 3,461,717 A | 8/1969 | Dunlap et al. |
| 5,323,655 A | 6/1994 | Eagan et al. |
| 5,456,118 A | 10/1995 | Hines et al. |
| 5,606,133 A | 2/1997 | Hines et al. |

(Continued)

FOREIGN PATENT DOCUMENTS

WO    WO 01/86251 A1    11/2001

*Primary Examiner*—Thomas P. Noland
(74) *Attorney, Agent, or Firm*—Alston & Bird LLP

(57) ABSTRACT

A gyratory compactor apparatus is provided for interacting with a sample within a generally cylindrical mold having a flange. Such an apparatus comprises a frame defining an axis and an offsetable member engaged with the frame for engaging one end of the mold. The offsetable member is displaceable from the axis and is concurrently movable in an orbital motion thereabout. A pressure ram is movable along the axis and a mold-engaging device is engaged with the frame for receiving the mold such that the mold and frame axes are coaxial. The pressure ram is axially movable within the mold to apply a compaction pressure on the sample, and thereby maintains a portion of the mold at a gyration point along the frame axis. The mold-engaging device axially moves the mold into engagement with the offsetable member. A securing device engaged with the offsetable member and movable therewith reversibly engages the mold to secure the mold to the offsetable member as the secured end is moved in the orbital motion by the offsetable member. The mold is thereby gyrated and dynamically maintained at a gyration angle. Associated apparatuses, devices, and methods are also provided.

2 Claims, 21 Drawing Sheets

U.S. PATENT DOCUMENTS

| | | |
|---|---|---|
| 5,698,789 A | 12/1997 | Lainio et al. |
| 5,817,946 A | 10/1998 | Brovold |
| 5,824,913 A * | 10/1998 | Pyle ............................ 73/818 |
| 5,939,642 A | 8/1999 | King et al. |
| 6,026,692 A | 2/2000 | Brovold |
| 6,205,864 B1 * | 3/2001 | Vialletel et al. ............... 73/824 |
| 6,477,783 B1 | 11/2002 | Harman et al. |
| 6,868,738 B2 * | 3/2005 | Moscrip et al. ............... 73/818 |
| 6,889,558 B2 | 5/2005 | Hines |
| 6,925,889 B2 | 8/2005 | Pyle et al. |
| 7,107,858 B2 * | 9/2006 | Brovold ........................ 73/818 |
| 2004/0020306 A1 | 2/2004 | Moscrip et al. |
| 2004/0079166 A1 * | 4/2004 | Moscrip et al. ................ 73/824 |
| 2005/0022608 A1 * | 2/2005 | Moscrip ....................... 73/818 |
| 2007/0017298 A1 * | 1/2007 | Verna et al. ................... 73/818 |

* cited by examiner

DEVICE FOR DETERMINING AND MAINTAINING MOLD GYRATION ANGLE IN A GYRATORY COMPACTOR

CROSS-REFERENCE TO RELATED APPLICATIONS

This application is a divisional of U.S. application Ser. No. 10/755,123, filed Jan. 9, 2004, now U.S. Pat. No. 7,121,149, which claims the benefit of U.S. Provisional Application No. 60/439,250, filed Jan. 10, 2003, which are hereby incorporated herein in their entirety by reference.

BACKGROUND OF THE INVENTION

1. Field of the Invention

The present invention relates to a gyratory compactor apparatus and, more particularly, to an improved gyratory compactor apparatus and associated devices and methods.

2. Description of Related Art

In order to measure certain physical properties, such as density, moisture content and compressive strength, of some materials, such as soil or paving material, loose samples of the soil or paving material are formed into test specimens under reproducible conditions using laboratory compaction machines. It is desirable to compact the test specimens under conditions that simulate actual use. For a paving material sample, this requires simulation of the kneading force applied to the paving material by the paving roller. Simply applying a compressive force to the sample does not adequately simulate the kneading action of the paving roller. As a result, compaction machines that gyrate the sample during compression have been developed to simulate actual conditions of use.

For example, a compaction machine which provides axial compression while gyrating the sample of soil or paving material so as to effectively knead the sample is illustrated in U.S. Pat. No. 5,323,655 to Eagan et al. The gyratory compactor described therein includes a ram applying compressive force from one end of a cylindrical mold, wherein the other end of the mold is gyrated by rotating a base supporting the other end of the mold.

Another example of a gyratory compactor apparatus is disclosed in U.S. Pat. No. 5,939,642 to King et al. The '642 patent describes a gyratory compactor apparatus design for facilitating ergonomics and efficiency, while improving consistency of operating parameters. The gyratory compactor described therein allows the user to slide the cylindrical compaction mold into the compaction chamber without the necessity of lifting the mold and includes an integral specimen removal ram. In addition, the frame design reduces frame deflection that could undesirably affect the angle of gyration. Further, the angle of gyration of the compactor apparatus can be changed by simply replacing a single component of the apparatus.

Notwithstanding the advances that have been made in the art of gyratory compactors, there is a need for smaller and less costly designs, with improved operational efficiency and accuracy. Additionally, there is a need for a gyratory compactor having improved ergonomics. For example, placement and removal of the mold containing the sample should be accomplished with minimal difficulty. Also, it would be advantageous to provide a compactor design that allows the user to quickly and easily change operating parameters, such as the angle of gyration. Further, there is a need in the art for a gyratory compactor that provides a constant angle of gyration during the compaction procedure with minimal deviation therefrom.

BRIEF SUMMARY OF THE INVENTION

The above and other needs are met by the present invention which, in one embodiment, provides a gyratory compactor apparatus adapted to interact with a generally cylindrical mold having an outer diameter, defining an axis, and adapted to have a sample disposed therein. The mold also includes opposed first and second ends and a radially extending flange having an outer diameter. Such a gyratory compactor apparatus comprises a frame defining an axis and a mold-engaging device adapted to receive the mold and to axially move the mold with respect to the frame. An offsetable member is operably engaged with the frame and configured to be capable of engaging the second end of the mold when the mold is axially moved into engagement with the offsetable member by the mold-engaging device. The mold-engaging device is then configured to release the mold such that the mold is independent thereof. The offsetable member is further configured to be capable of being displaced from the frame axis and concurrently movable in an orbital motion about the frame axis. A portion of the mold away from the second end is maintained at a gyration point along the frame axis and, as the second end of the mold is moved in the orbital motion, the mold is gyrated and capable of being dynamically maintained at a gyration angle related to the displacement of the offsetable member, the gyration point, and the frame axis.

Another advantageous aspect of the present invention comprises a gyratory compactor apparatus adapted to interact with a generally cylindrical mold having an outer diameter, defining an axis, and adapted to have a sample disposed therein. The mold also includes opposed first and second ends and a radially extending flange having an outer diameter. Such a gyratory compactor apparatus includes a frame defining an axis and an offsetable member operably engaged with the frame and configured to be capable of engaging the second end of the mold. The offsetable member is further configured to be capable of being displaced from the frame axis and concurrently movable in an orbital motion about the frame axis. A pressure ram is operably and movably engaged with the frame and configured to be capable of moving along the frame axis. A mold-engaging device is operably engaged with the frame and adapted to receive the mold such that the mold axis corresponds to the frame axis and such that the pressure ram is capable of moving axially within the mold to apply a compaction pressure on the sample within the mold. The pressure ram thereby maintains a portion of the mold at a gyration point along the frame axis. The mold-engaging device is further configured to axially move the second end of the mold into engagement with the offsetable member and to then release the mold such that the mold is independent thereof. A securing device is operably engaged with the offsetable member and is movable therewith, wherein the securing device is configured to reversibly engage the second end of the mold so as to secure the second end of the mold to the offsetable member as the second end of the mold is moved in the orbital motion by the offsetable member. The mold is thereby gyrated and capable of being dynamically maintained at a gyration angle related to the displacement of the offsetable member, the gyration point, and the frame axis.

Still another advantageous aspect of the present invention comprises a gyratory compactor apparatus adapted to interact with a generally cylindrical mold having an outer diameter, defining an axis, and adapted to have a sample disposed therein. The mold also includes opposed first and second ends and a radially extending flange having an outer diameter. Such a gyratory compactor apparatus includes a frame defining an axis and configured to receive the mold. A pressure ram is operably and movably engaged with the frame and configured to be capable of moving along the axis thereof. The pressure ram is further capable of being received by and operably engaging the mold through the first end, and moving within the mold to apply a compaction pressure on the sample within the mold. The pressure ram thereby maintains a portion of the mold at a gyration point along the frame axis. An offsetable member is operably engaged with the frame and is configured to be capable of engaging the second end of the mold. The offsetable member is further configured to be capable of being displaced from the frame axis and concurrently movable in an orbital motion about the frame axis, such that the second end of the mold is moved in the orbital motion. The mold is thereby gyrated and is capable of being dynamically maintained at a gyration angle related to the displacement of the offsetable member, the gyration point, and the frame axis.

Yet another advantageous aspect of the present invention comprises a gyratory compactor apparatus defining an axis. Such an apparatus includes a pressure ram configured to be capable of moving along the apparatus axis and a rotatable member configured to be rotatable about the apparatus axis. A mold is capable of being disposed between the pressure ram and the rotatable member and is adapted to have a sample disposed therein. The mold is generally cylindrical, defines an axis, and has opposed first and second ends. The mold is configured to receive the pressure ram therein through the first end so as to apply a compaction pressure on the sample within the mold, wherein the pressure ram thereby maintains a portion of the mold at the gyration point along the apparatus axis. The second end of the mold defines a radiused bearing surface extending about an inner circumference thereof. An offsetable member is operably engaged with the rotatable member and defines a radiused bearing surface complementarily corresponding to the second end bearing surface of the mold. The offsetable member bearing surface is capable of movably engaging the second end bearing surface of the mold. The offsetable member is further configured to be displaceable with respect to the rotatable member from the apparatus axis so as to cause the second end of the mold to orbit about the apparatus axis when the offsetable member is rotated by the rotatable member. The mold is thereby gyrated at a gyration angle related to the displacement of the offsetable member, the gyration point, and the apparatus axis.

Yet still another advantageous aspect of the present invention comprises a device adapted to interact with a generally cylindrical mold for a gyratory compactor apparatus defining an axis. The mold has an outer diameter, defines an axis, and is adapted to have a sample disposed therein. The mold also has opposed first and second ends and a radially extending flange having an outer diameter. Such a device includes a movable mounting plate configured to be movable between a first position and a second position along the apparatus axis. A pair of pivoting members is pivotably mounted to the movable mounting plate along parallel pivot axes. A support rail mounted is to each pivoting member. The support rails are laterally separated by less than the outer diameter of the flange with the movable mounting plate in the first position, such that the support rails are capable of supporting the mold by the flange. The pivoting members pivot between the first and second positions such that, with the movable mounting plate in the second position, the support rails are separated by more than the outer diameter of the flange and are thereby incapable of supporting the mold by the flange.

Still another advantageous aspect of the present invention comprises a pressure-measuring device adapted for use with a gyratory compactor apparatus. Such a device includes a pressure-bearing member and an elongate stem member defining an axis. The stem member includes a first end operably engaged with the pressure-bearing member and an opposing second end. An elongate sleeve is configured to extend concentrically over the stem member and in close relation thereto so as to be capable of slidably engaging the stem member over an extended engagement length. The sleeve has a first end extending toward the pressure-bearing member, when the sleeve is engaged with the stem member, and an opposing second end. A load-determining device is in communication with the sleeve such that load-determining device is axially fixed with respect to the sleeve. The load-determining device is further configured to be in communication with the stem member so as to measure an actual axial load exerted on the pressure-bearing member via the stem member.

Yet another advantageous aspect of the present invention comprises a device adapted to determine and maintain an angle of gyration of a mold engaged with a gyratory compactor apparatus defining an axis. The mold is generally cylindrical, defines an axis, and has opposed first and second ends. The mold is gyratable about the apparatus axis at a gyration point displaced from the second end toward the first end. Such a device includes an offsetable member adapted to be capable of engaging the second end of the mold in displacement from the apparatus axis and to be movable in an orbital motion about the apparatus axis so as to cause the mold to gyrate with respect to the gyration point, wherein the gyration point remotely disposed with respect to the second end of the mold. A sensor device is configured to dynamically determine an actual angle of gyration of the mold, wherein the actual angle of gyration is related to the displacement of the offsetable member, the gyration point, and the apparatus axis. A controller is operably engaged with the offsetable member so as to be capable of directing adjustment of the displacement of the offsetable member to provide a desired angle of gyration with respect to the gyration point. The controller is in communication with the sensor device and is responsive thereto so as to be capable of dynamically adjusting the displacement of the offsetable member to maintain the actual angle of gyration substantially equal to the desired angle of gyration.

Another advantageous aspect of the present invention comprises a gyratory compactor apparatus defining an axis. Such a gyratory compactor apparatus includes a sample-manipulating device adapted to receive a mold having a sample disposed therein, wherein the sample-manipulating device is configured so as to be capable of gyrating the mold while applying a compaction pressure to the sample. A frame member supports the sample-manipulating device, and has at least one component formed of a laminated sheet material.

Yet another advantageous aspect of the present invention comprises a cleaning device adapted to remove sample residue from a gyratory compactor apparatus defining an axis. The gyratory compactor apparatus is further adapted to have an offsetable member operably engaged with a rotatable member configured to be rotatable about the axis. The offsetable member is further adapted to be capable of engaging an end of a mold having a gyration point away from the end, and to be capable of being displaced from the axis so as to cause the mold to gyrate with respect to the gyration point when the offsetable member is rotated about the axis by the rotatable member. Such a cleaning device includes a plate having a first face supporting the rotatable member, wherein the plate is configured to be non-rotatable about the axis. The plate has a second face opposing the first face and defines a groove in the first face disposed radially outward of the rotatable member, wherein the groove is configured to collect the sample residue. The plate further defines a channel extending from the groove toward the second face, wherein the channel is configured to facilitate removal of the sample residue from the gyratory compactor. A sweeping member is configured to orbit about the axis in operable engagement with the groove defined by the plate so as to move the sample residue along the groove and to direct the sample residue to the channel for removal.

Another advantageous aspect of the present invention comprises a method of manufacturing a gyratory compactor apparatus, wherein the gyratory compactor apparatus includes a frame having a plurality of components. First, the components are operably engaged with a jig configured to align the components in a desired relationship. The components are then secured together so as to form the frame, wherein the frame defines an axis and has alignment members operably engaged therewith. Thereafter, the frame is removed from the jig. A sample-manipulating device having a plurality of components is then operably engaged with the frame, wherein the sample-manipulating device is adapted to receive a mold capable of receiving a sample therein and is configured so as to be capable of gyrating the mold while applying a compaction pressure to the sample. The components of the sample-manipulating device have alignment members, corresponding to the frame alignment members, operably engaged therewith so as to facilitate alignment of the sample-manipulating device with respect to the axis when the sample-manipulating device is operably engaged with the frame.

Thus, embodiments of the present invention provide significant advantages as detailed further herein.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

Figure 13:
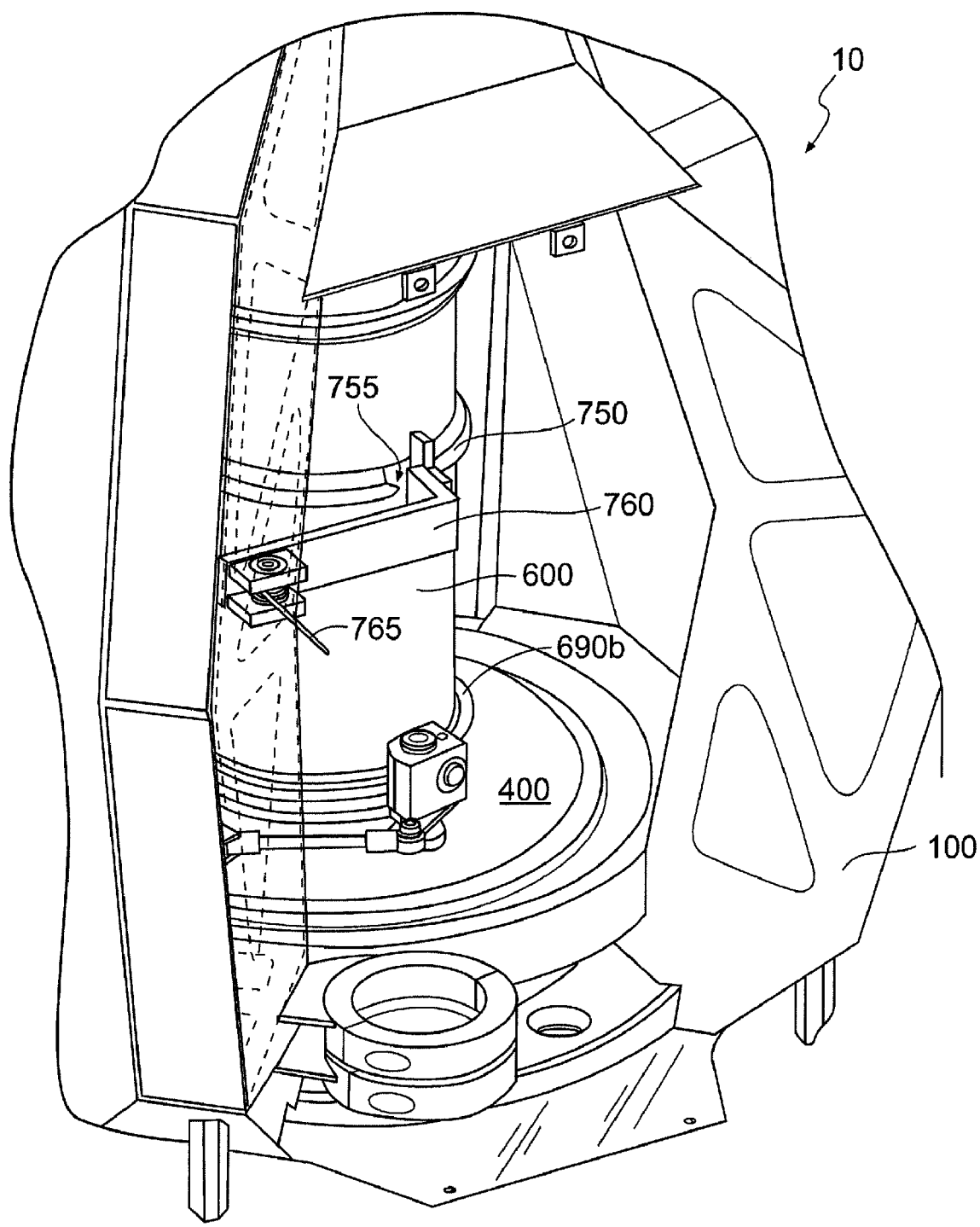
Figure 14A:
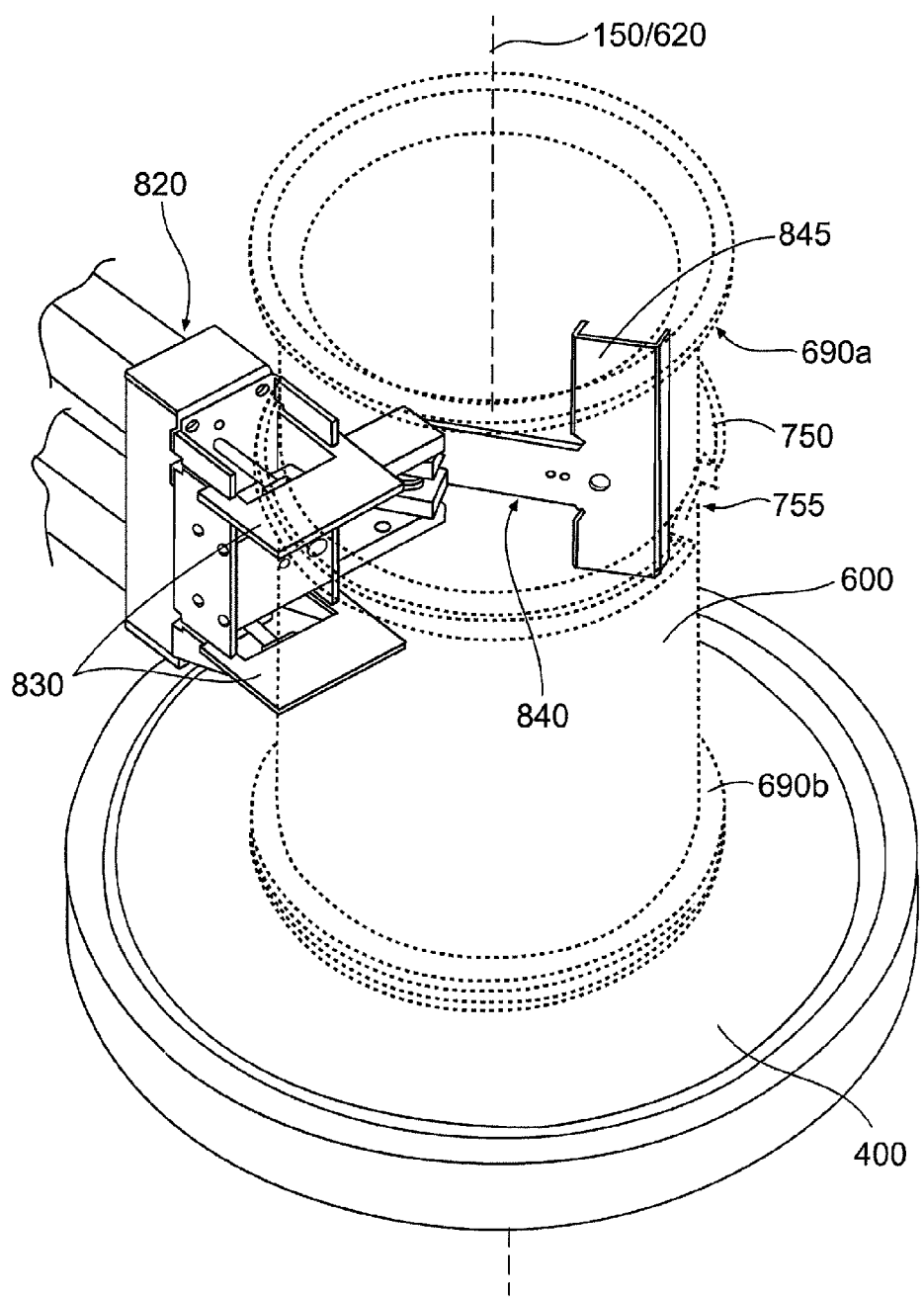
Figure 14B:
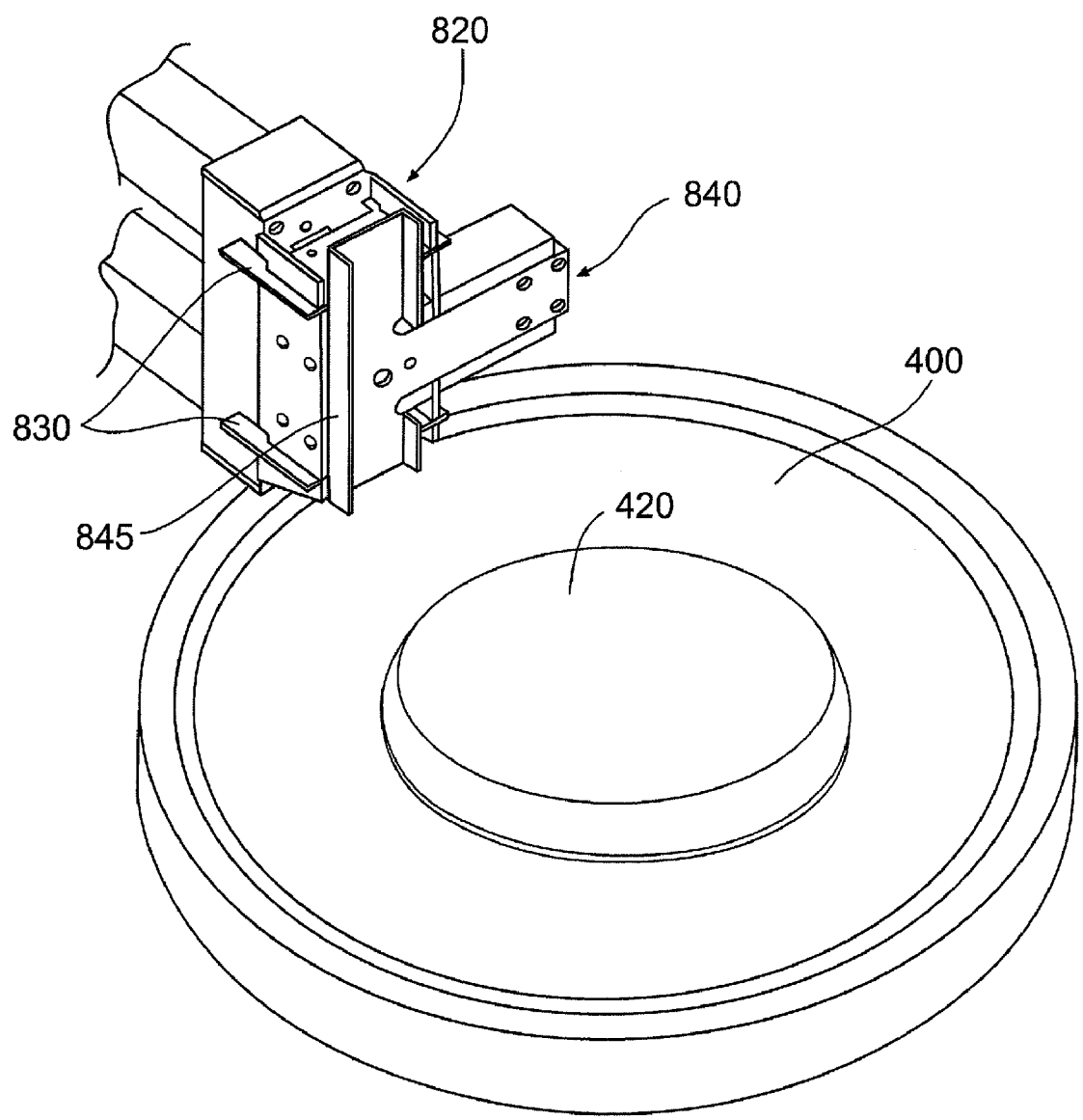

FIG. 13 is a schematic of a mold-securing mechanism and an anti-rotation device, both configured to interact with a mold for a gyratory compactor apparatus according to one embodiment of the present invention; and FIGS. 14A and 14B are schematics of an external mold angle sensing device implementing contact type sensors to determine the gyration angle of a mold for a gyratory compactor apparatus according to another embodiment of the present invention.

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

FIGS. 1-10B illustrate various aspects of a gyratory compactor apparatus according to one embodiment of the present invention, the apparatus being indicated generally by the numeral 10. Such an apparatus 10 generally comprises a frame 100 defining an axis 150. The frame 100 is configured to have a pressure ram 200 engaged therewith, wherein the pressure ram 200 is capable of moving along the axis 150. Opposing the pressure ram 200 is a rotatable member 300 that is also aligned with the axis 150 and is rotatable thereabout. Disposed between the pressure ram 200 and the rotatable member 300 is an offsetable member 400. In cooperation with the frame 100, the general area between the pressure ram 200 and the offsetable member 400 defines a mold well 500 configured to accept a mold 600. The apparatus 10 further includes a mold-handling device 700 configured to receive and manipulate the mold 600 within the mold well 500. The apparatus 10 also has incorporated therewith a control system 800 configured to interact with the mold 600 when the mold 600 is received in the mold well 500.

In one advantageous embodiment of the present invention, the frame 100 is comprised of a plurality of components 110 fastened together, for example, by fasteners, by adhesive, by welding, or in any other suitable manner consistent with the spirit and scope of the present invention. As one skilled in the art will appreciate, and as further discussed herein, accurate and precise alignment of the components is critical to the operation of the apparatus 10, wherein such alignment must be maintained in both static and dynamic states. As such, a variety of stresses are imparted to the frame 100 during the gyratory compaction process, thereby further requiring that some of the frame components 110 be configured to handle different stresses than some other components 110. In addition, one of the parameters which must also be considered in the design and construction of the apparatus 10 is the weight thereof.

Figure 8:
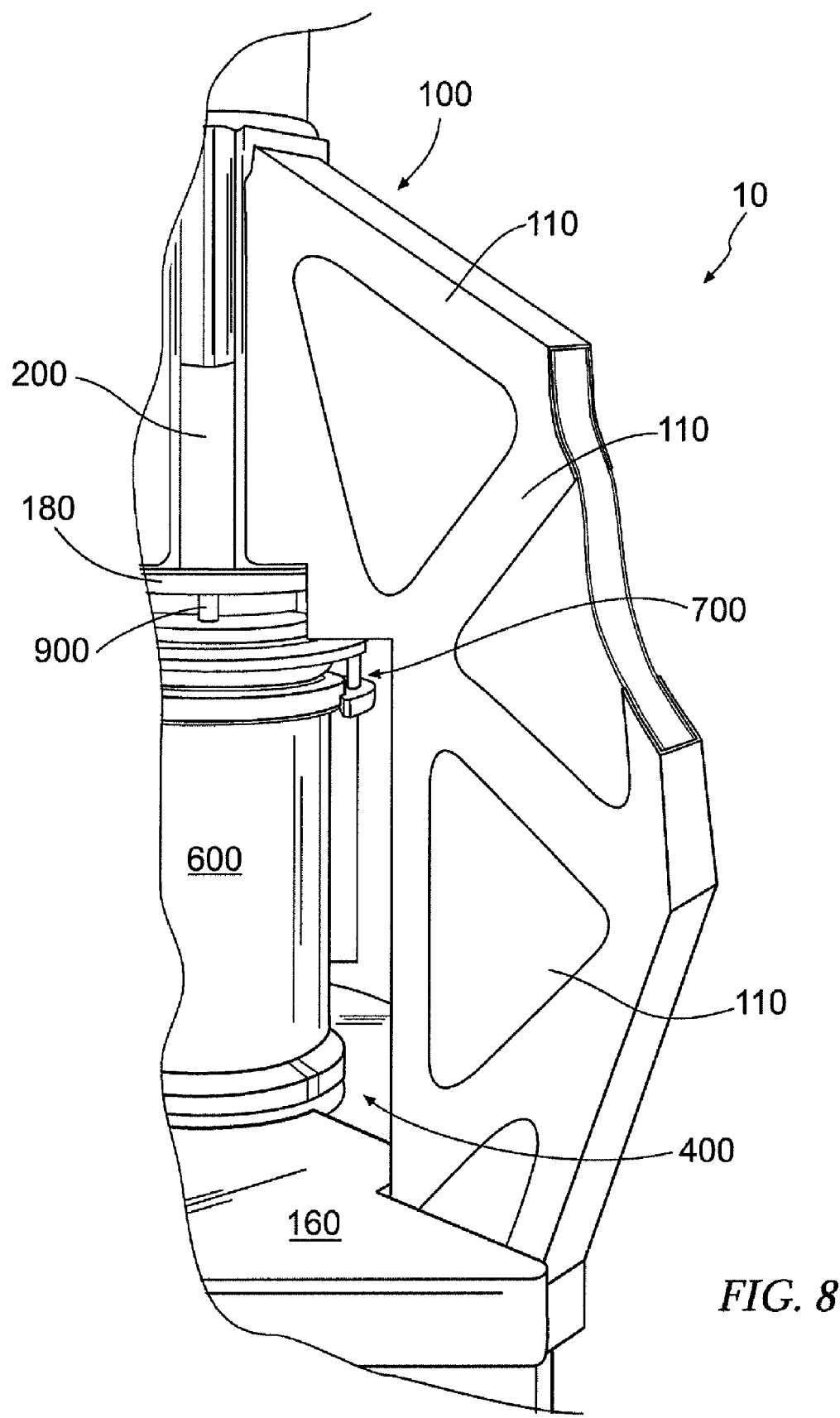
FIG. 8 is a schematic cutaway view of a gyratory compactor apparatus according to one embodiment of the present invention illustrating a composite construction of the frame of the gyratory compactor apparatus.

Accordingly, it is advantageous to be able to customize the configuration of, rigidify, and/or reinforce particular frame components 110 where necessary, while minimizing the number of components 110, in order to optimize the configuration of the frame 100. Therefore, some advantageous embodiments of the present invention utilize one or more components 110 having a composite construction. For example, FIG. 8 illustrates a component 110 constructed of individual members, with one or more of those members comprising two coplanar metal sheets joined together by welding, adhesive, fasteners, or in any other suitable manner. That is, one of those members may be configured such that any wall, side, or otherwise defining surface may be comprised of at least two coplanar sheets secured together. However, the illustrated construction of the component 110 is not intended to be limiting since one skilled in the art will readily appreciate that the composite construction of a component 110 may include more than two sheets and may also include sheets comprised of many different materials, such as metals, polymers, or even other composites. In addition, the composite construction may also be selectively applied such as, for example, where only spot reinforcing is necessary for a component 110, such that only a portion of a component 110 may include the described composite construction. Further, other measures may also be implemented to prevent the adjacent sheets of the composite from moving with respect to each other where, for example, the adjacent sheets may include interlocking tabs or other mechanical structures (not shown) for minimizing or preventing such relative movement. Thus, embodiments of the present invention utilizing composite construction will realize significant savings in the weight of the frame 100, whereby the configuration of the frame 100 can be optimized with a minimum of components 100 without sacrificing the strength necessary for withstanding the stresses imparted thereto during operation of the apparatus 10.

As previously described, accurate and precise alignment of its components is critical to the operation of the apparatus 10 where, as further described herein, such components are discrete with respect to the frame 100 and must be assembled therewith in order to obtain a functional apparatus 10. Heretofore, assembly of a gyratory compactor apparatus typically required a trained technician, sophisticated alignment tools, and specific procedures for the gyratory compactor to be properly assembled and suitably aligned. Such measures would often need to be duplicated if the gyratory compactor was disassembled for maintenance or to be moved. The disadvantages of those requirements and procedures should be readily apparent to one skilled in the art. Accordingly, other advantageous embodiments of the present invention implement an alignment procedure into the manufacturing process for the frame 100 and, in some instances, other components of the apparatus 10. More particularly, during the manufacturing process for the frame 100, one or more components 110 are engaged with one or more jigs (not shown), each of which is specifically configured to hold and align the components 110 in a specific relationship. The specific relationship typically corresponds to the determination of the frame axis 150, though other references related to the apparatus 10 may also associated with a particular jig. One or more of the components 110 may also have one or more alignment members (not shown) attached thereto or otherwise associated therewith, or the alignment members may be formed through cooperation between components 110.

While in the jig, the components 110 may be secured together, for example, by welding, with adhesives, with fasteners, or the like to form the frame 100 or a subassembly thereof. In instances where the entire frame 100 is formed in the jig, the components 110 forming the frame 100 will be properly aligned when the completed frame 100 is removed from the jig. In addition, the alignment members will then serve to align the frame 100 with the other components that are attached to the frame 100 to form the apparatus 10. Where a subassembly of the frame 100 is formed by the components 110 in the jig, that subassembly will be properly aligned when removed from the jig, while the alignment members will serve to align that subassembly with respect to the frame 100, or one or more of the other components attached to the frame 100, to form the apparatus 10. In some embodiments, the other components attached to the frame 100 to form the apparatus 10 may also have alignment members (not shown) corresponding to and capable of interacting with the alignment members associated with the frame 100. As such, through the use of the jig and, in some instances, the alignment members, the need for a trained technician and special alignment tools and procedures during the gyratory compactor assembly or reassembly process is minimized or eliminated, while also reducing the time and expense associated with an extensive and complicated assembly or reassembly process.

As shown in FIGS. 1-3, 5, 6A, and 7, the frame 100 is configured to receive the pressure ram 200 such that the pressure ram is capable of moving along the axis 150 to provide an axial compressive force with respect to the mold 600 received by the apparatus 10. Accordingly, the mold 600 which, in one instance, has a cylindrical inner surface, must engage the apparatus 10 such that the pressure ram 200 can extend through the first end 610 of the mold 600 and exert the necessary axial compressive force along the longitudinal axis 620 of the mold 600. However, the mold 600 must also be gyrated simultaneously with the application of the axial compressive force in order to achieve and simulate the rolling of the paving roller or other compaction device over a material surface. In order to achieve the necessary gyration of the mold 600, the second end 630 is typically laterally displaced such that the longitudinal axis 620 is tilted by a particular angle 640 (otherwise referred to herein as the mold angle, the angle of gyration, or the gyration angle) with respect to the axis 150 defined by the travel of the pressure ram 200, as shown, for example, in FIG. 2. As the axial compressive force is applied along the axis 150 by the pressure ram 200, the laterally displaced second end 630 of the mold 600 is moved in an orbital motion about the axis 150. Since the mold 600, away from the second end 630 and toward the first end 610, is constrained about the axis 150 by the pressure ram 200, the orbital motion of the second end 630 about the axis 150 thus causes the mold 600 to gyrate within the apparatus 10. This operational characteristic or the apparatus 10 is otherwise referred to herein as the "gyratory compaction" process for the sample 50.

According to one advantageous embodiment of the present invention, as shown in FIGS. 2, 3, and 5-7, the gyratory compactor apparatus 10 further includes an offsetable member 400 operably engaged with the frame 100, in generally opposing relation to the pressure ram 200. The frame 100, the pressure ram 200, and the offsetable member 400 thereby cooperate to define the mold well 500 capable of receiving the mold 600 therein. The offsetable member 400 is capable of being laterally displaced from the axis 150 so as to cooperate with the pressure ram 200 and the mold 600 to define the gyration angle 640 about a gyration point 650. The gyration point 650 generally corresponds to the center point 210 of the end of the pressure ram 200 (described further herein as the foot portion 245) opposing the offsetable member 400, or may otherwise be defined as the point of intersection of the longitudinal axis 620 of the mold 600 and the axis 150 of the frame 100.

In order for the mold 600 to gyrate as required, the offsetable member 400 further includes a bearing member 420 engaged therewith. The bearing member 420 is generally configured as a truncated hemisphere having a flat surface 430 and a circumferential bearing surface 440 with an arcuate profile. The arcuate profile of the bearing surface 440, in one instance, may be defined by a radius, though the arcuate profile of the bearing surface 440 may be configured in many different manners as required. Accordingly, the second end 630 of the mold 600 also includes a bearing surface 660 centered about the longitudinal axis 620 and complementarily configured with respect to the bearing surface 440 of the bearing member 420. When the bearing surfaces 440, 660 are engaged, a ball and socket joint is essentially formed, whereby the second end 630 of the mold 600 is essentially constrained, but allowed to pivot about the gyration center 410 (otherwise referred to herein as the center of gyration of the second end 630 of the mold 600) of the bearing member 420 as the mold 600 is gyrated, the gyration center 410 therefore being disposed along the longitudinal axis 620 of the mold 600. The gyration center 410 corresponds to the center point of a sphere overlaid on and corresponding to the truncated hemisphere forming the bearing member 420. Accordingly, since mold 600 gyrates about the bearing member 420 and since the bearing member 420 also functions to constrain the second end 630 of the mold 600, the lateral displacement of the gyration center 410 of the bearing member 420 from the frame axis 150 the may readily determined. Thus, both the gyration angle 640 and the gyration point 650 may, in turn, be readily determined in a static mode, as well as in a dynamic mode during operation of the apparatus 10.

Once laterally displaced from the frame axis 150, the offsetable member 400/bearing member 420 must be moved in an orbital motion about the frame axis 150 in order to provide the necessary gyration for the mold 600. Thus, in one embodiment of the present invention, the offsetable member 400 is engaged with and/or supported by the rotatable member 300, wherein the rotatable member 300 is configured to be rotatable about the frame axis 150. The offsetable member 400 is thus configured to be laterally displaceable with respect to the rotatable member 300. The rotatable member 300 is further engaged with and/or supported by a non-rotatable plate 320, as shown, for example, in FIGS. 5 and 7, wherein the plate 320 may be engaged with or an integral component of the frame 100. The plate 320 has a first face 330 directed toward the rotatable member 300 and an opposing second face 340. In one embodiment, the plate 320 may also be configured to define a groove 350 extending through the first face 330 and disposed radially outward of the rotatable member 300. In such instances, the groove 350 may further include one or more channels 360 extending from the groove 350 toward the second face 340 of the plate 320.

Since the offsetable member 400 may interact closely with the sample 50, residue from the sample 50 may undesirably gather about the offsetable member 400 and the rotatable member 300 in some embodiments, particularly when the offsetable member 400 and the rotatable member 300 are disposed at the lower end of the mold well 500. Accordingly, in such instances, the groove 350 is provided to collect the sample residue, while the one or more channels 360 is provided to direct the sample residue outwardly of the apparatus 10 from the groove 350. Also provided is a sweeping member 370 which, in one embodiment, is engaged with the rotatable member 300 so as to be rotatable therewith in engagement with the groove 350. The sweeping member 370 is further configured to have a profile generally corresponding to the cross-sectional shape of the groove 350 such that, as the sweeping member 370 is drawn around the groove 350 by the rotating rotatable member 300, sample residue in the groove 350 is directed into the one or more channels 360 and thus outwardly of the apparatus 10. In some embodiments, the sweeping member 370 is also configured so as not to interfere with the offsetable member 400 as the offsetable member 400 is laterally displaced with respect to the rotatable member 300. Accordingly, the sweeping member 370 is capable of cooperating with the groove 350 and the one or more channels 360 to remove sample residue from the mold well 500 as the apparatus 10 is operated, thereby reducing or eliminating the need to manually remove sample residue from the mold well 500 when the apparatus 10 is idle.

Figure 6A:
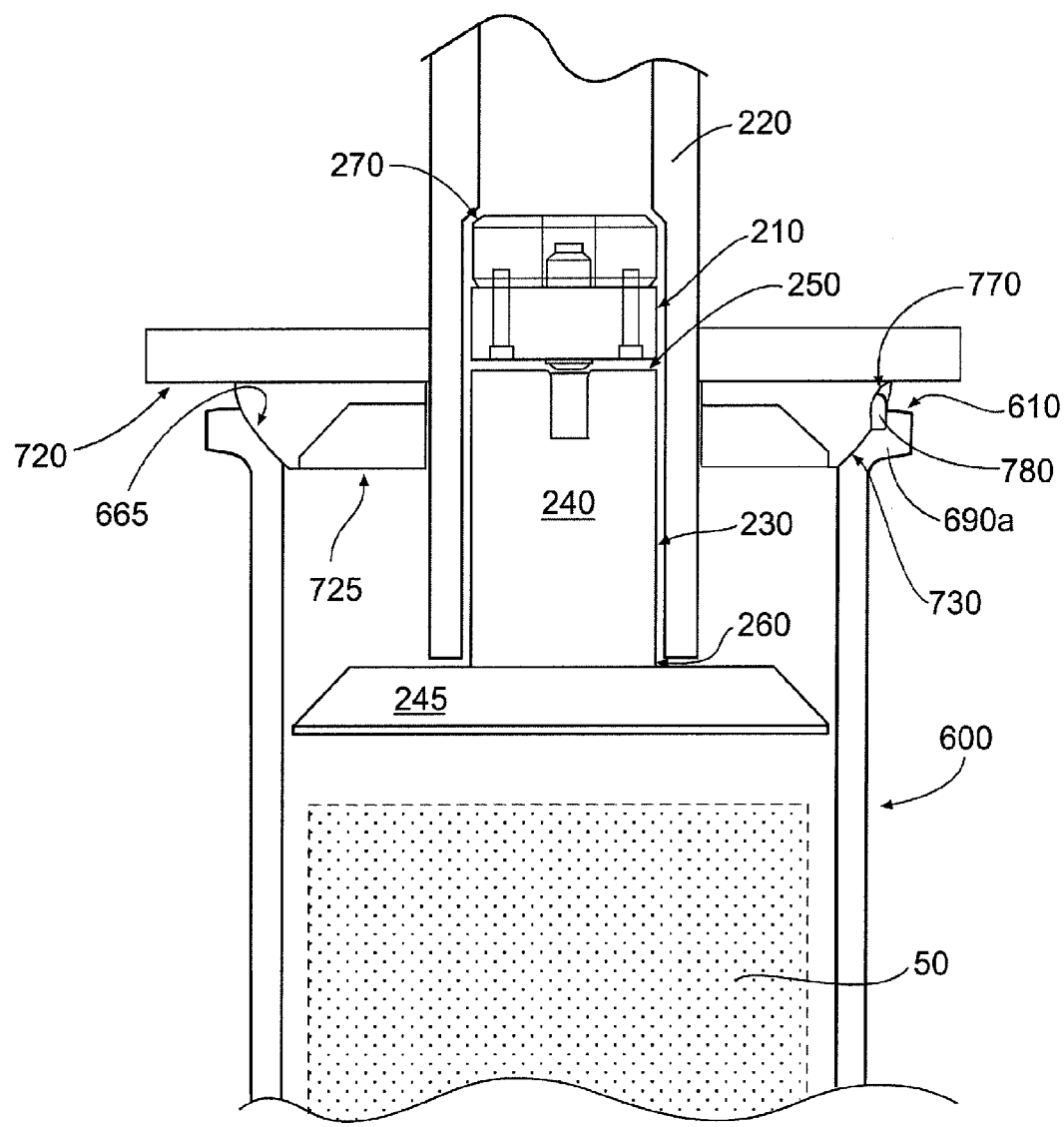
FIG. 6A is a schematic of an axial-load focusing load cell configuration implemented in conjunction with a mold-securing mechanism to interact with a mold for a gyratory compactor apparatus according to one embodiment of the present invention.

As previously discussed, one of the purposes of a gyratory compactor apparatus 10 is to impart an axial compressive force on the sample 50 as the sample 50 is being gyrated. The necessary axial compressive force is thus provided by the pressure ram 200, as shown in FIG. 6A, that is engaged with the frame 100 and configured to provide the compressive force along the axis 150. It is also typically desirable for the value of the axial compressive force to be accurately measured and such a measurement is generally accomplished through the use of a load cell. However, a load cell may indicate an inaccurate value if subjected to an eccentric or non-axial applied load where, in a gyratory compactor, such eccentric forces may be generated as the mold is gyrated. Accordingly, one advantageous aspect of the present invention comprises a load cell 210 engaged between the ram tube 220 and the ram head 230 of the pressure ram 200, whereby the ram tube 220 is configured to receive, with close tolerance, a cylindrical portion 240 of the ram head 230 therein such that the ram tube 220 interacts with the cylindrical portion 240 over an extended length. A first end 250 of the cylindrical portion 240 extends into the ram tube 220, while a second end 260 is directed outwardly thereof.

The load cell 210 is disposed within the ram tube 220 so as to interact with the first end 250 of the cylindrical portion 240. Though the load cell 210 is shown to directly interact with the first end 250, indirect interaction such as, for example, in instances where a spacer (not shown) is disposed therebetween, is also suitable. The load cell 210 is preferably disposed as close to the first end 250 as possible. In addition, the load cell 210 is preferably securely constrained from movement along the axis of the ram tube 220 away from the ram head 230. For example, the ram tube 220 may include a mounting member 270 constrained from axial movement along the ram tube 220 away from the ram head 230 by a change in diameter of the ram tube 220, or by any other suitable mechanism. The load cell 210 is secured to the mounting member 270 and is thus firmly secured within the ram tube 220. Pressure exerted on the sample 50 by the ram head 230 is thereby transmitted by the cylindrical portion 240 to the load cell 210 which, as will be readily appreciated by one skilled in the art, allows the pressure applied to the sample 50 to be determined. However, the extended interaction length and the close tolerance between the ram tube 220 and the cylindrical portion 240 of the ram head 230, according to advantageous aspects of the present invention, serves to dissipate any eccentric forces transmitted to the ram head 230 through the ram tube 220, during gyration of the mold 600. Accordingly, any eccentric forces acting on the ram head 230 will not be transmitted to the load cell 210.

The load cell 210 thereby experiences only a focused axial load from the ram head 230, and the load cell 210 configured according to embodiments of the present invention will thus more accurately indicate the axial compressive force exerted on the sample 50 by the pressure ram 200 during the gyratory compaction process. One skilled in the art will also appreciate that the axial compressive force applied on the sample 50 may also be determined in other ways such as described, for example, in U.S. patent application Ser. No. 10/210,020, also assigned to the assignee of the present invention, entitled "Method and Apparatus for Determining the Angle of Gyration and/or the Pressure in a Gyratory Compactor" and filed on Jul. 31, 2002, which is incorporated herein by reference.

Figure 6B:
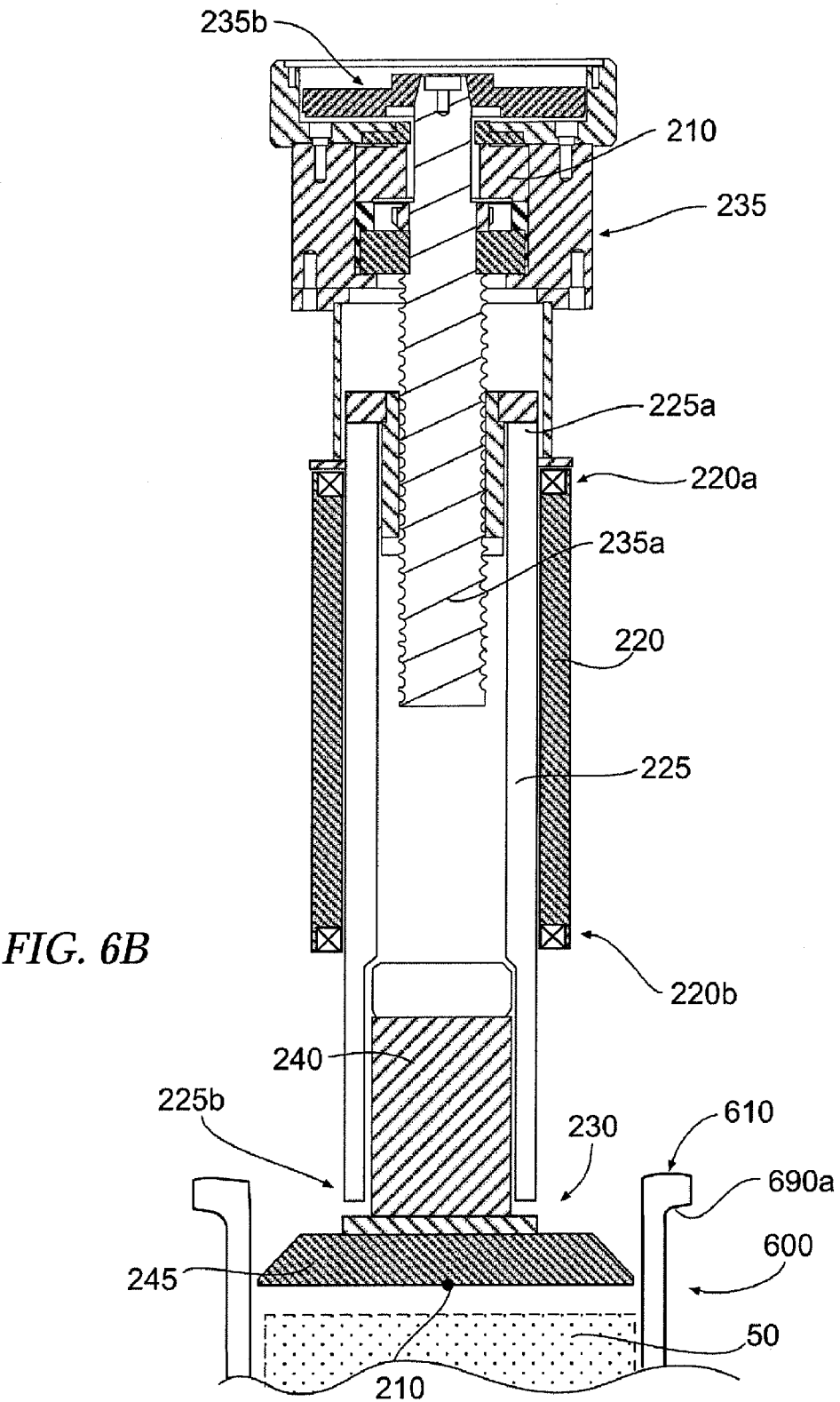
FIG. 6B is a schematic of an axial-load focusing load cell configuration implemented to interact with a mold for a gyratory compactor apparatus according to another embodiment of the present invention.
Figure 7:
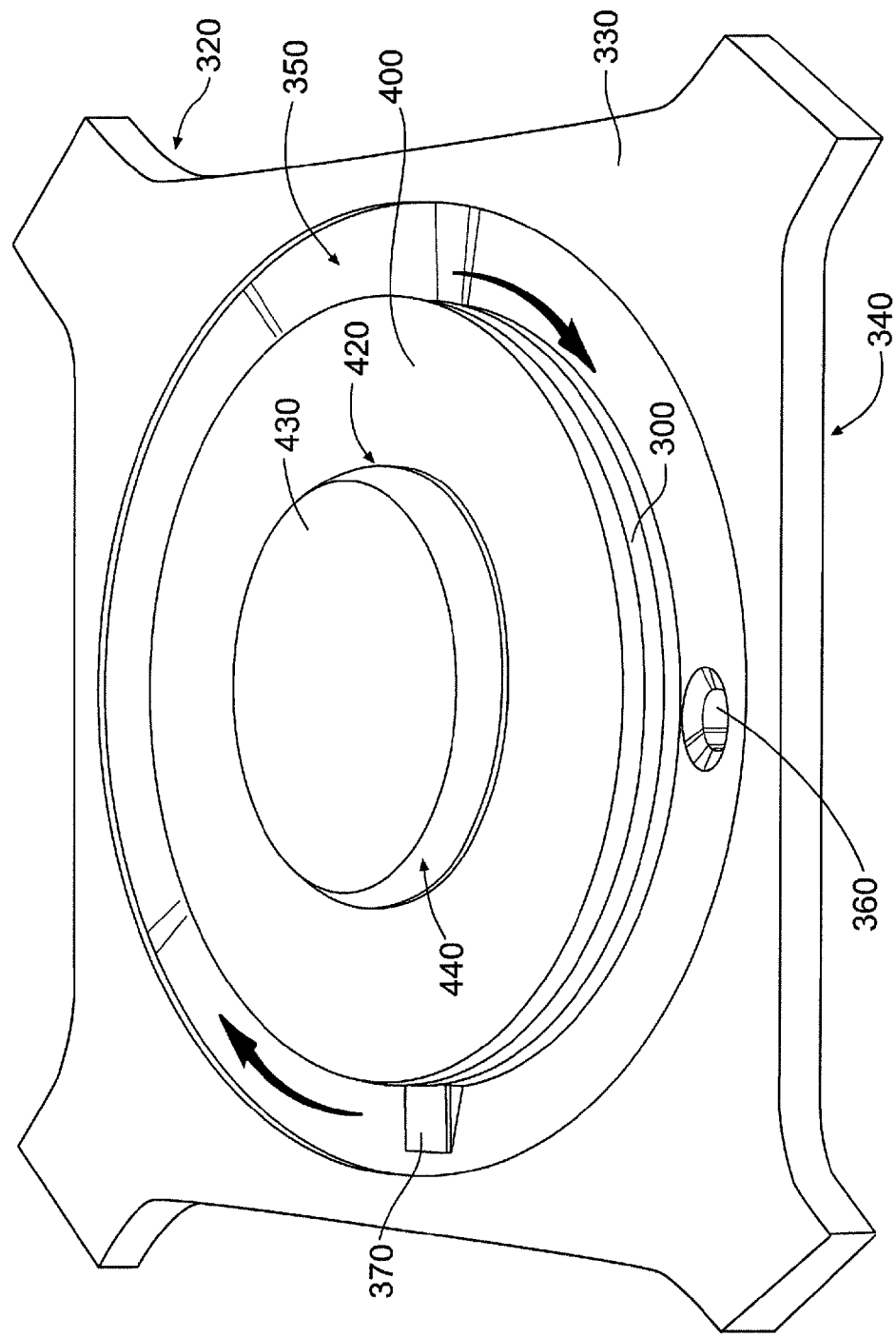
FIG. 7 is a schematic of a cleaning mechanism implemented in conjunction with an offsetable member supported by a rotatable member and configured to interact with a mold for a gyratory compactor apparatus according to one embodiment of the present invention.

One skilled in the art will also appreciate that the pressure ram 200, as shown in FIG. 6A, may have different operating mechanisms for applying the desired compaction pressure. Further, the load cell 210 may be remotely displaced with respect to the ram head 230. For example, the configuration previously described may include a hydraulic system (not shown) for forcing the ram head 230 out of the ram tube 220 to provide the compaction pressure. FIG. 6B illustrates another example of a mechanism for applying compaction pressure via the pressure ram 200. As shown, the ram tube 220 may be configured to receive a ram shaft 225 therein through the proximal end 220b thereof, wherein the ram shaft 225 includes opposing ends 225a, 225b. The end 225b of the ram shaft 225 disposed outwardly of the ram tube 220 is configured to receive the cylindrical portion 240 of the ram head 230. The opposing end 225a of the ram shaft 225 includes internal threads (the end of the ram shaft 225 may be threaded or the ram shaft 225 may include a nut member operably engaged therewith) and is configured to receive a screw portion 235a of a screw drive mechanism 235 engaged with the distal end 220a of the ram tube 220. Note, however, that the screw drive mechanism 235 may be engaged with the ram tube 220 and ram shaft 225 in many different manners than the embodiment described herein. The load cell 210, in this instance, is remotely disposed with respect to the ram head 230 and is engaged with the drive portion 235b of the screw drive mechanism 235 such that the axial pressure generated by the screw drive mechanism 235 against the ram shaft 225, and thus the ram head 230, is measured. Accordingly, as before, an extended interaction length and close tolerance between the ram tube 220 and the ram shaft 225 serves to dissipate any eccentric forces transmitted to the load cell 210 via the drive portion 235b of the screw drive mechanism 235 during gyration of the mold 600. Accordingly, any eccentric forces acting on the ram head 230 will not be transmitted to the load cell 210, and the load cell 210 will experience only a focused axial load from the ram head 230. The load cell 210 will thus more accurately indicate the axial compressive force exerted on the sample 50 by the pressure ram 200 during the gyratory compaction process.

Figure 1:
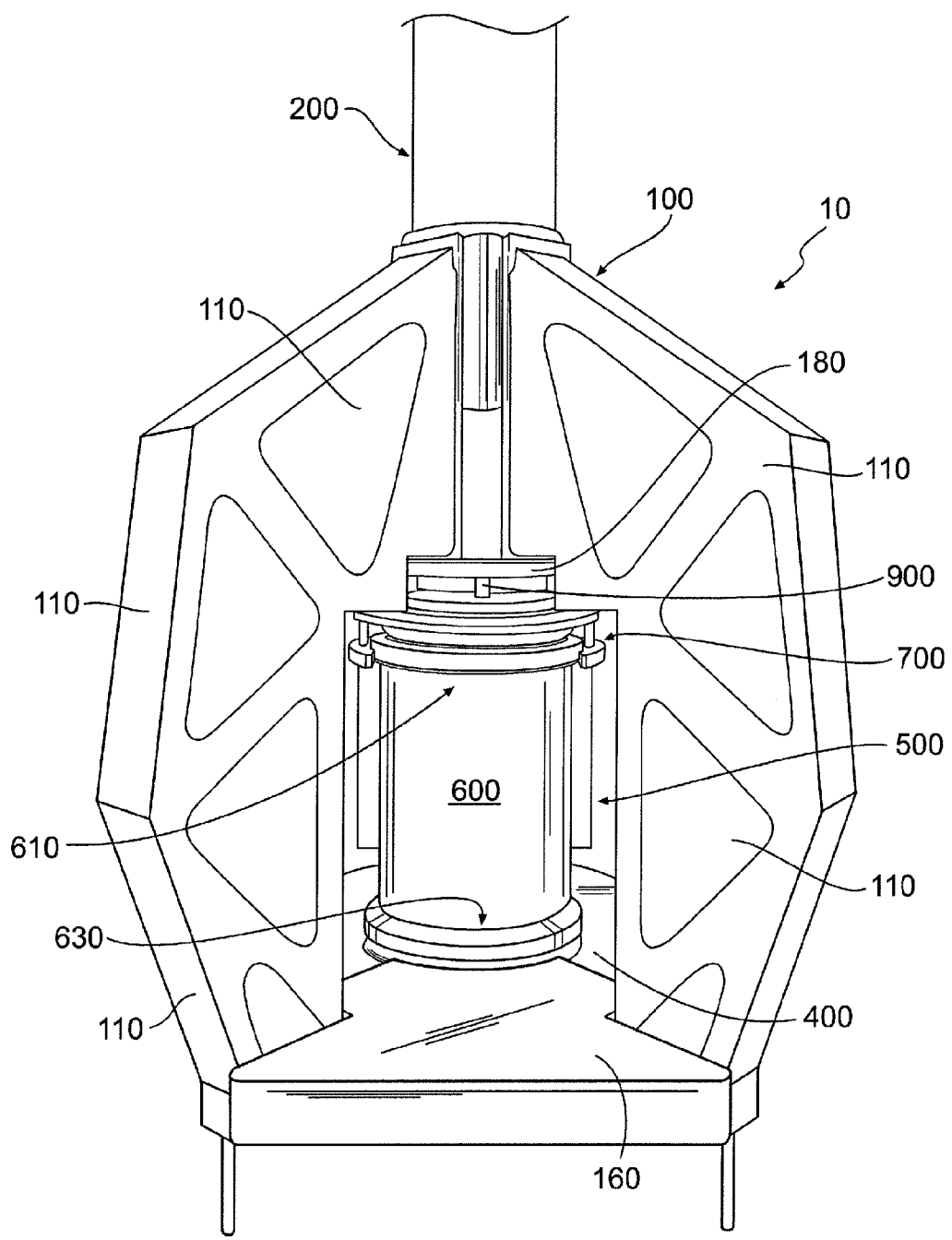
FIG. 1 is a schematic of a gyratory compactor apparatus according to one embodiment of the present invention.
Figure 2:
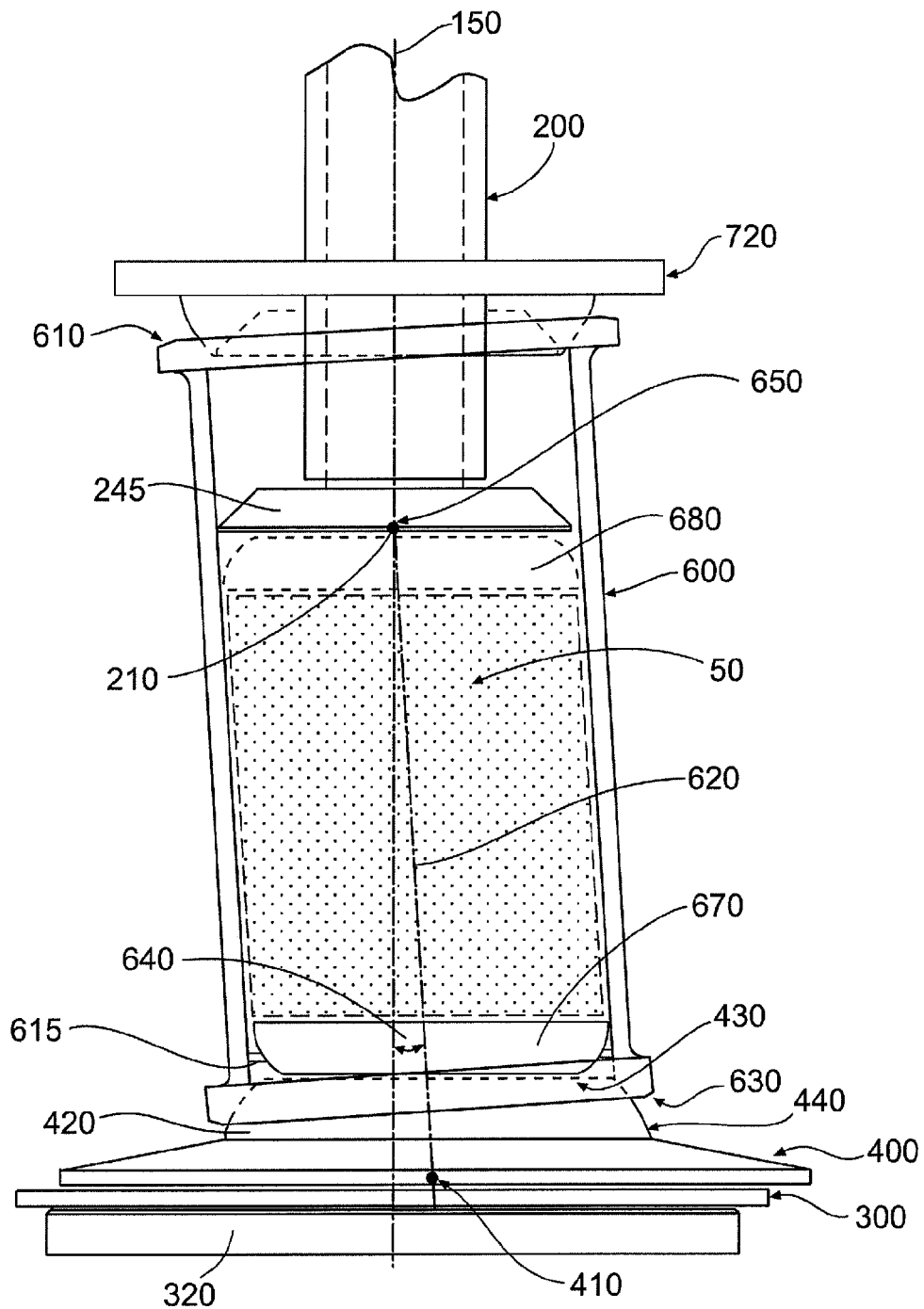
FIG. 2 is a schematic of a gyration angle of a mold engaged with a gyratory compactor apparatus according to one embodiment of the present invention.

As shown in FIG. 2, the apparatus 10 further includes a first puck 670 capable of being disposed within the mold 600 toward the second end 630 thereof. The mold 600 and/or the first puck 670 are configured such that the first puck 670 is temporarily retained toward the second end 630 so as to cooperate with the mold 600 to contain the sample 50. For example, the first puck 670 may be temporarily retained in place within the mold 600 by a ring 615 engaged with the inner surface of the mold 600 so as to retain the sample 50 in the mold 600 as the mold 600 is inserted into or removed from the mold well 500. Upon application of the compressive force by the pressure ram 200, the first puck 670 moves along the mold 600 and into contact with the flat surface 430 of the bearing member 420. The ram head 230 of the pressure ram 200 also includes a foot portion 245 attached to the second end 260 of the cylindrical portion 240 or ram shaft 225 outwardly of the ram tube 220. In some instances, the foot portion 245 functions as a "puck" and opposes the first puck 670 within the mold 600, whereby the sample 50 is disposed therebetween and inside the mold 600. In other instances, a second puck 680 (shown in phantom) may be disposed within the mold 600 between the foot portion 245 of the pressure ram 200 and the sample 50 such that the foot portion 245 does not directly interact with the sample 50. However, as previously discussed, the center point 210 of the foot portion 245 defines the gyration point 650 of the mold 600 and the foot portion 245 moves closer to the bearing member 420 as the sample 50 is compacted during the gyratory compaction process. Accordingly, the foot portion 245 may be described as "inactive" since the first end 610 of the mold 600 is not constrained to provide a fixed gyration point 650 and since the foot portion 245 is not capable of laterally translating in order to maintain the gyration angle 640 as the sample 50 is compacted. As such, the gyration angle 640, which is typically required remain constant at a specified value during the compaction process, will change as the sample 50 is compacted.

Figure 3:
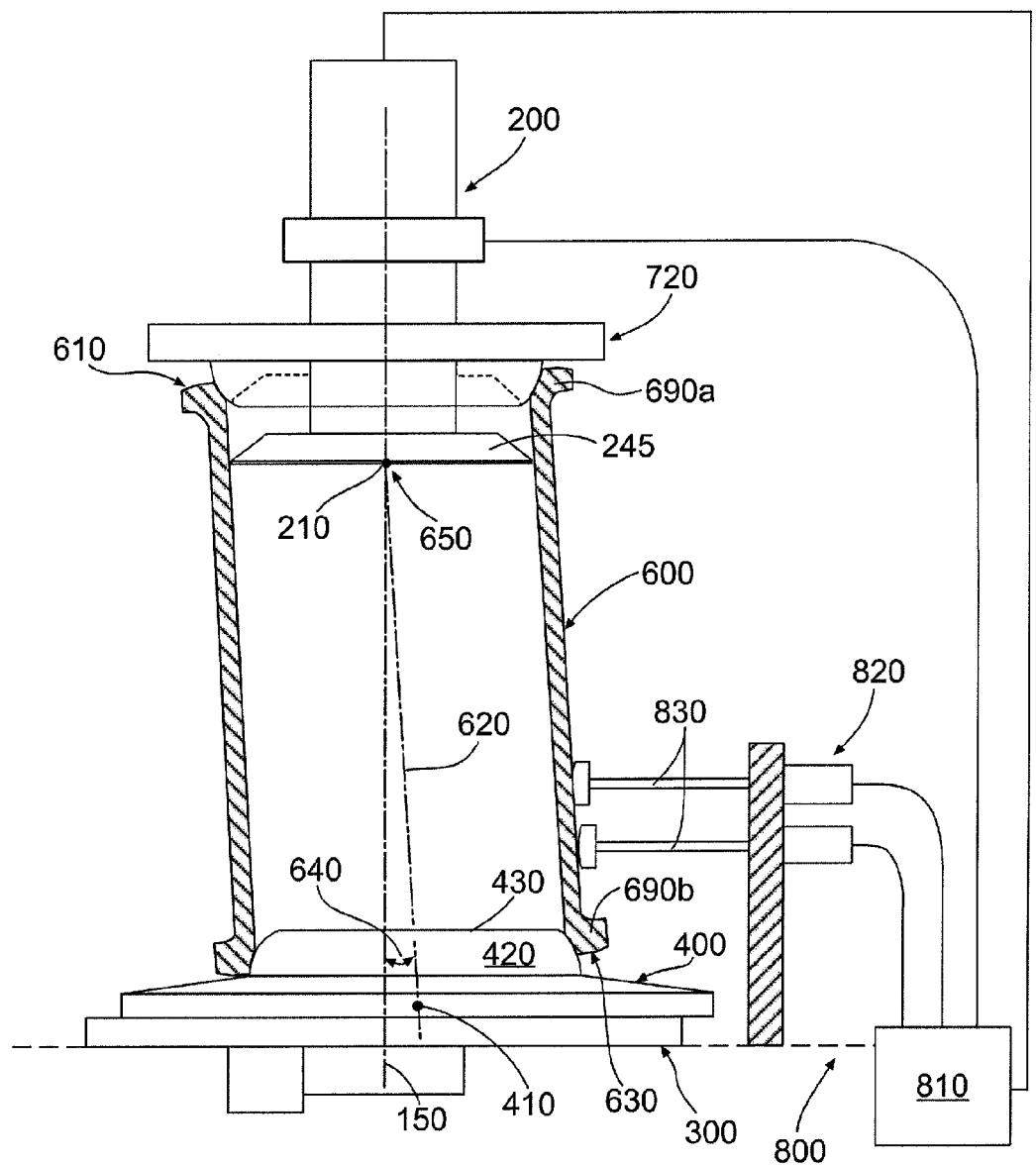
FIG. 3 is a schematic of a mold angle sensing device in communication with a controller for providing a closed-loop control system for a mold engaged with a gyratory compactor apparatus according to one embodiment of the present invention.
Figure 4:
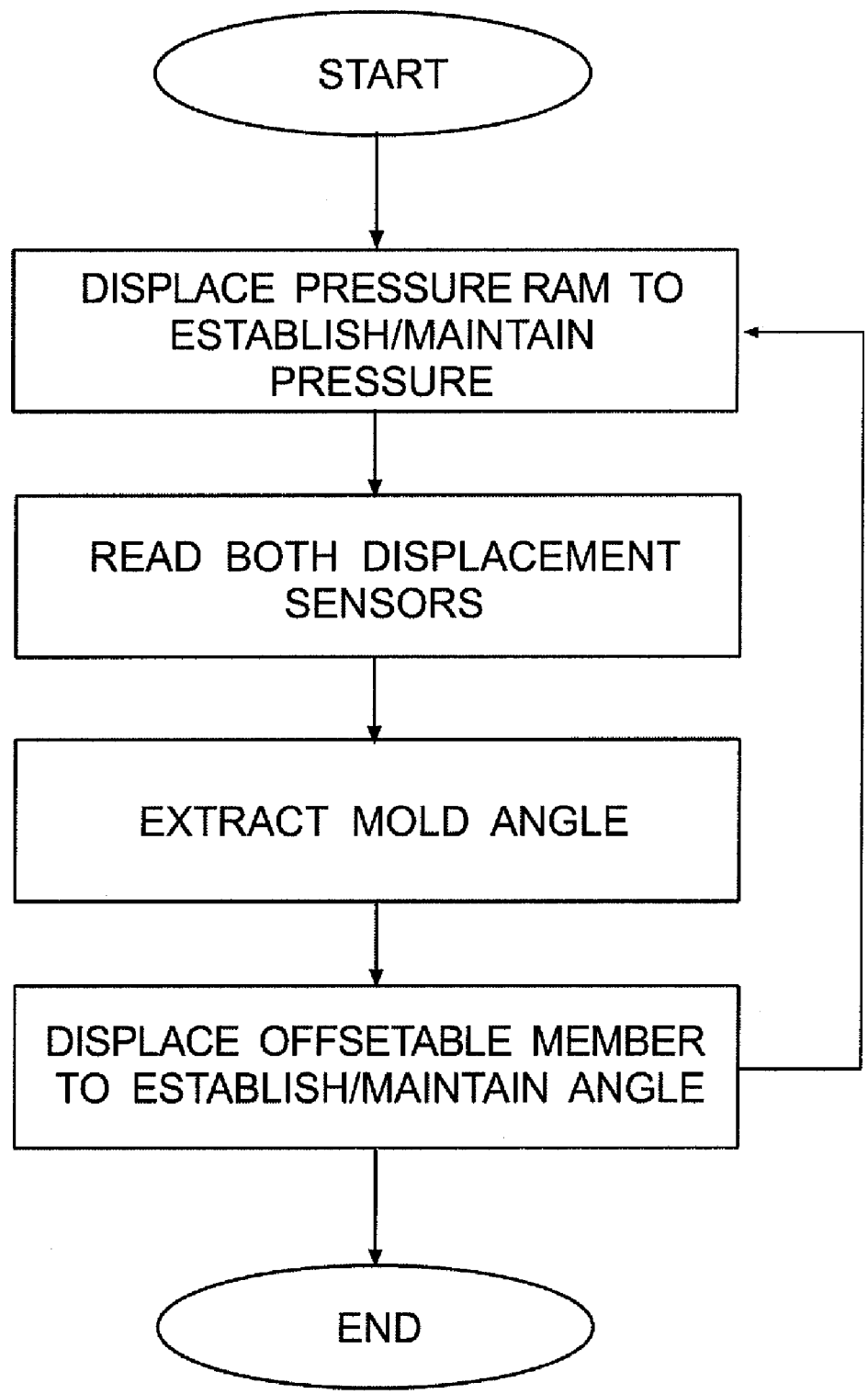
FIG. 4 is a flow diagram of a gyratory compaction procedure implemented by a closed-loop control system according to one embodiment of the present invention.
Figure 5:
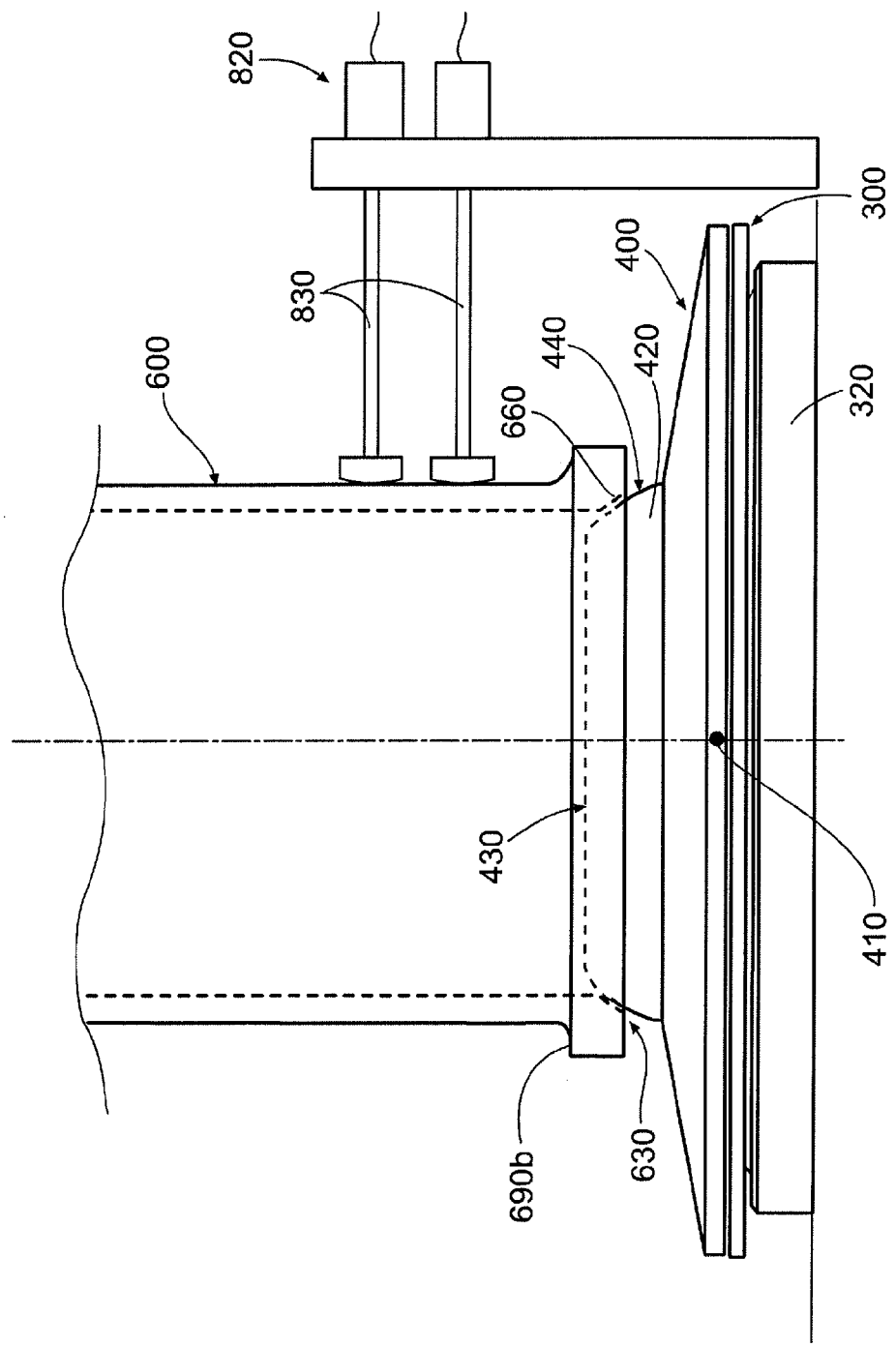
FIG. 5 is a schematic of an external mold angle sensing device implementing contact type sensors to determine the gyration angle of a mold for a gyratory compactor apparatus according to one embodiment of the present invention.

As a result, advantageous embodiments of the present invention also implement a closed loop control system 800, as shown, for example, in FIGS. 3 and 4, for continuously monitoring the gyration angle 640 and dynamically adjusting the lateral displacement of the offsetable member 400 during the gyratory compaction process so as to maintain the specified value of the gyration angle 640 as the sample 50 is compacted. More particularly, the control system 800 comprises a controller 810 and a mold angle sensing device 820. The mold angle sensing device 820, as shown in FIG. 5, includes a pair of sensors 830 aligned with and separated by a distance along the frame axis 150. The sensors 830 are configured to interact with the exterior surface of the mold 600 and may be, for example, contact sensors, proximity sensors, or any other suitable contacting or non-contacting sensors or combinations thereof, wherein one skilled in the art will readily appreciate that the gyration angle 640 of the mold 600 may be determined from the difference in the absolute distances between each of the sensors 830 and the exterior surface of the mold 600. However, in some instances, the gyration angle 640 may be determined from inside the mold 600 using, for example, a device for determining the angle of the mold as also disclosed in U.S. patent application Ser. No. 10/210,020, previously incorporated herein by reference. One skilled in the art will also appreciate that the gyration angle 640 may also be determined in other manners such as, for example, longitudinally along the mold 600.

The sensors 830 are in communication with the controller 810, wherein the controller 810 is configured to direct the displacement of the pressure ram 200, and thus the foot portion 245, into the mold 600 so as to establish the specified axial compression force on the sample 50 as measured, for example, by the load cell 210. The controller 810 is also configured to read the displacement or proximity values indicated by the sensors 830 and to determine the actual mold angle 640. The controller 810 is further capable of comparing the actual mold angle 640 to the specified or desired mold angle and then directing the adjustment of the lateral displacement of the offsetable member 400 until the desired mold angle is attained. The controller 810, in some instances, is configured to simultaneously measure, and adjust if necessary, both the compression force on the sample 50 and the mold angle 640. In other instances, the measurements and any necessary adjustments may be performed at spaced intervals or may be performed with such frequency that the compaction force and mold angle 640 are maintained in approximately real time. One skilled in the art will also readily appreciate that the controller 810 may take many different forms depending at least partially on the complexity of the required parameter control for the apparatus 10 as well as the degree of automation or user friendliness desired by the end user. Further, though the determination of the gyration angle 640 is described herein in terms of a lateral displacement of the offsetable member 400, it will be understood that the control of the position of the offsetable member 400 may be accomplished in different manners such as, for instance, according to a Cartesian coordinate system and using, for example, an x-y table. In some embodiments of the present invention, a polar coordinate system is implemented via a polar excursion table which uses two parallel and concentric plates (the offsetable member 400 and the rotatable member 300), whereby the offsetable member 400 is translated according to the polar coordinate system into an eccentric position with respect to the rotatable member 300, as both are rotated about the axis 150. However, the example presented herein are not intended to be limiting since many other configurations of the apparatus 10 may be provided that are capable of providing the necessary lateral displacement of the second end 630 of the mold 600 as well imparting the required orbital motion of the second end 630 about the axis 150 in order to produce the gyration of the mold 600.

The ergonomics of the apparatus 10 are also considered in embodiments of the present invention. For example, the mold 600 having the puck 670 and sample 50 disposed therein may be heavy and cumbersome. Thus, it would be advantageous to minimize the handling necessary to load the mold 600 into the mold well 500 and to align the mold 600 with the bearing member 420 and the pressure ram 200. According to advantageous embodiments of the present invention, the apparatus 10 is further provided with a mold-handling device 700, as shown, for example, in FIGS. 9A-9C, for receiving and handling the mold 600 within the mold well 500. Initially, the mold 600 must be inserted into the mold well 500 and the second end 630 then lowered into engagement with the bearing member 420. As such, the frame 100 further includes a staging member 160 configured to receive the mold 600 thereon on a level such that the second end 630 is above the level of the flat surface 430 of the bearing member 420. Each end 610, 630 of the generally cylindrical mold 600 may also include a flange 690a, 690b (the mold 600 may include either or both of the flanges 690a, 690b, as appropriate for any embodiment of the invention as disclosed herein) extending radially outward therefrom to an outer diameter greater than the outer diameter of the mold 600. In one embodiment, the flange 690a at the first end 610 of the mold 600 includes a pair of flat portions 695a formed therein such that the flat portions 695a are separated by a distance less than the outer diameter of the flange 690a and such that each of the flat portions 695a are separated from the first end 610 of the mold 600 by a lip portion 695b of the flange 690a.

Figure 9A:
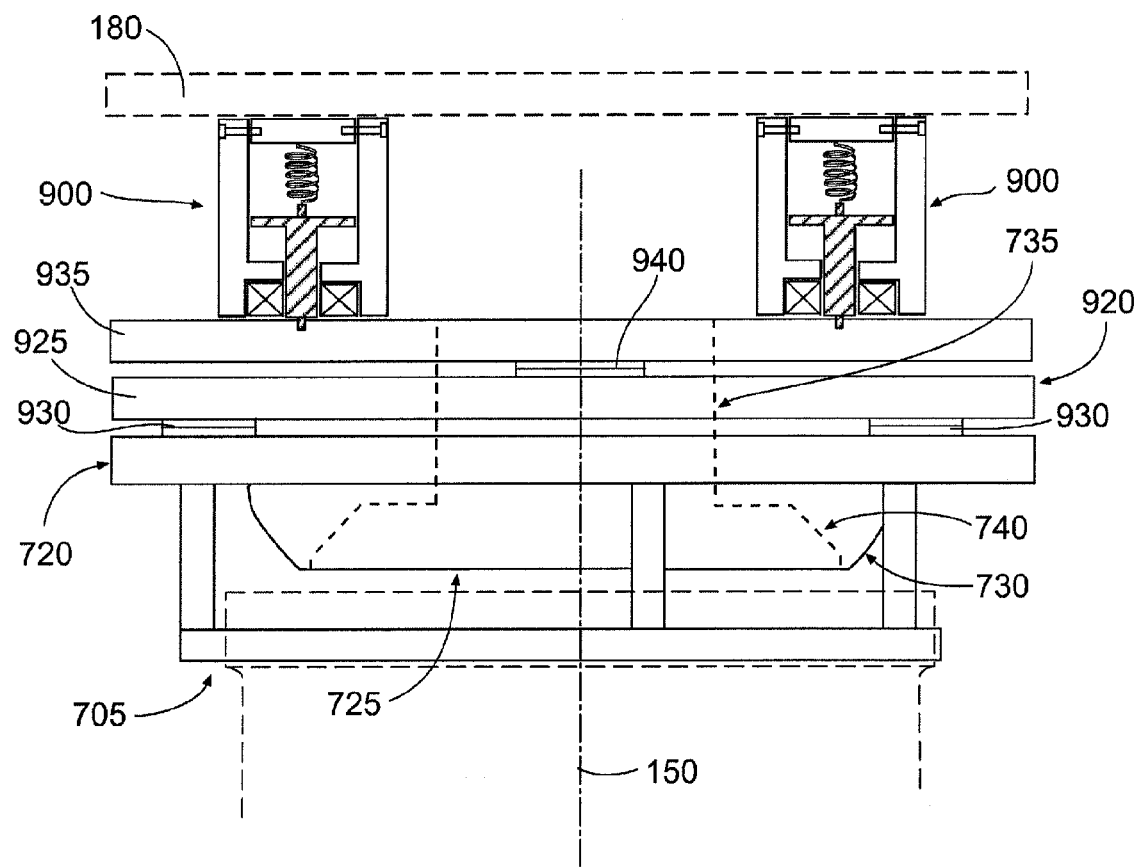
FIGS. 9A and 9B are schematics of a mold-handling device configured to manipulate a mold for a gyratory compactor apparatus according to one embodiment of the present invention.
Figure 9B:
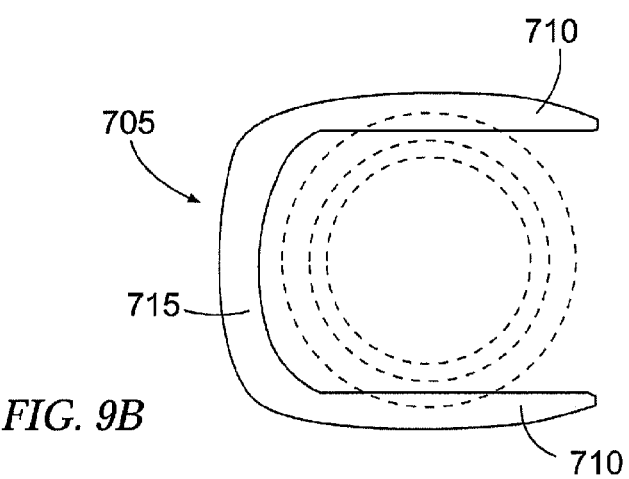
Figure 9C:
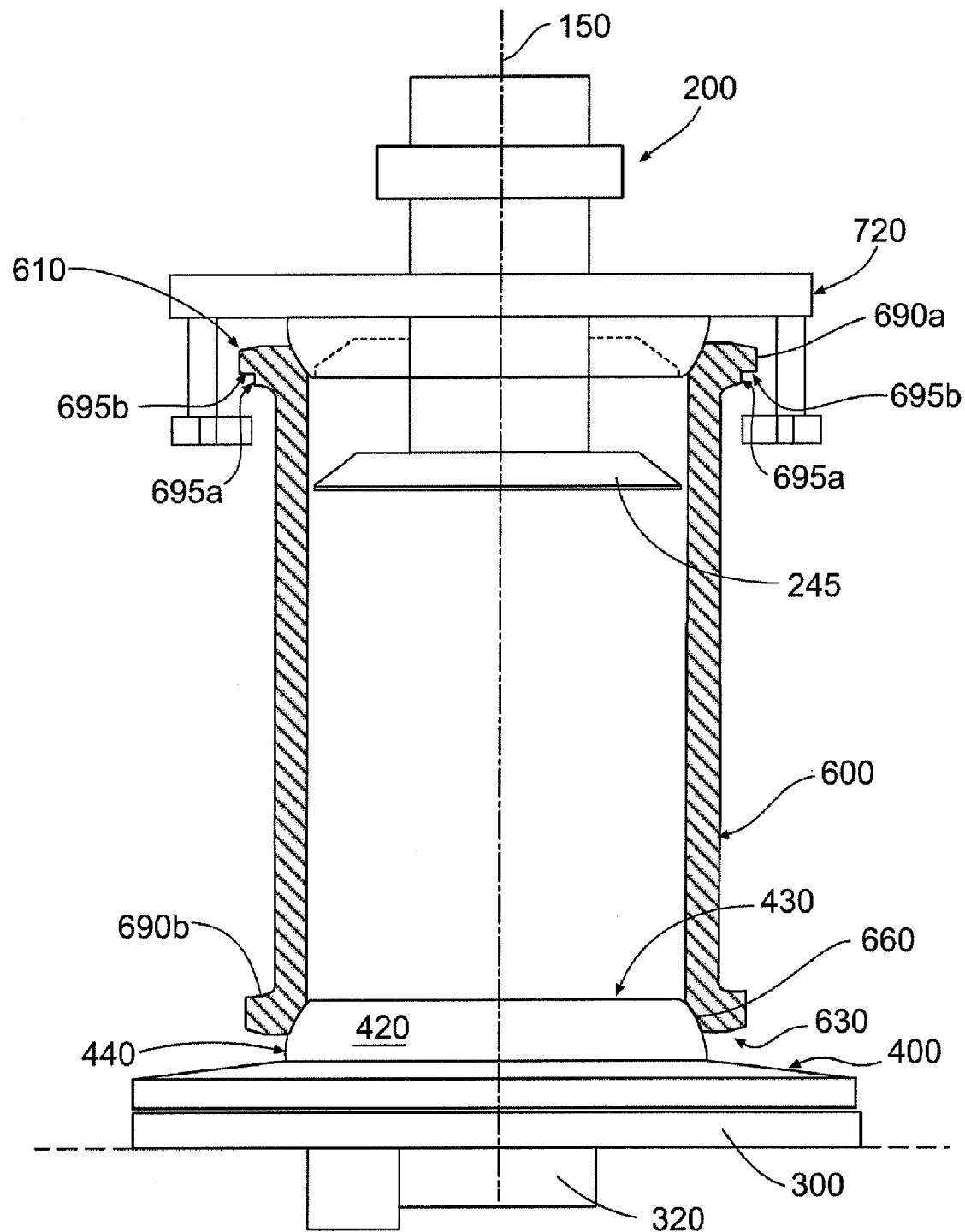
FIG. 9C is a schematic of a mold-handling device cooperating with an offsetable member to gyrate a mold with a gyratory compactor apparatus according to one embodiment of the present invention.

As shown in FIG. 9B, a receiving fork 705, generally comprising a pair of spaced apart tines 710 attached to a transversely-extending support member 715, is disposed toward the pressure ram end of the mold well 500, as shown in FIGS. 9A and 9C. In one embodiment, the receiving fork 705 is operably engaged with the frame 100 and is axially movable in cooperation with the pressure ram 200 along the frame axis 150, as discussed further below. The fork 705 is configured such that, when the mold 600 is placed on the staging member 160 and slid toward the mold well 500, the first end 610 of the mold 600 clears the foot portion 245 of the pressure ram 200 and the flat portions 695a of the flange 690a are received between the tines 710. Accordingly, the tines 710 and the flat portions 695a cooperate to ensure that the mold 600 is received in the mold well 500 is a desired rotational orientation. The support member 715 may be further configured to cooperate with the tines 710 so as to properly align the mold 600 within the mold well 500, such that the mold axis 620 is coaxial with the frame axis 150, when the mold 600 is received within the fork 705. The proper alignment may be ensured in many different manners such as, for example, through the mechanical configuration of the fork 705 or via an appropriate sensor (not shown) configured to sense when the mold 600 is received in the desired position. When the mold 600 is properly inserted into the fork 705, the mold 600 is no longer supported by the staging member 160, but instead is suspended above the bearing member 420 and supported by the lip portions 695b of the flange 690a on the tines 710 of the fork 705.

Once the mold 600 is inserted into the fork 705, the pressure ram 200 can be directed by the controller 810 to move toward the bearing member 420. As a result, the fork 705 will also move toward the bearing member 420, thereby lowering the second end 630 of the mold 600 into engagement with the bearing member 420. The fork 705 also moves axially along the mold 600, away from the flat portions 695a and the lip portions 695b of the flange 690a, when the mold 600 is sufficiently lowered so as to be supported by the bearing member 420. Further advancement of the pressure ram 200 causes the foot portion 245 to enter the first end 610 of the mold 600, and still further advancement of the pressure ram 200 is capable of providing the necessary axial compressive force on the sample 50, whereafter the gyration angle 640 may then be subsequently established.

In some instances, the mold-handling device 700 may further include a securing device 720 engaged with the fork 705 and configured to maintain the second end 630 of the mold 600 in sufficient contact with the bearing member 420 during the gyratory compaction process. The securing device 720 and the first end 610 of the mold 600 are configured similarly to the bearing member 420/second end 630 configuration previously discussed. That is, the securing device 720 is generally configured as a truncated hemisphere having an inner end 725 and a circumferential bearing surface 730 having an arcuate profile. Accordingly, the first end 610 of the mold 600 also includes a bearing surface 665 centered about the longitudinal axis 620 and complementarily configured with respect to the bearing surface 730 of the securing device 720. When the bearing surfaces 665, 730 are engaged, a ball and socket joint is essentially formed, whereby the first end 610 of the mold 600 is capable of pivoting about the securing device 720 as the mold 600 is gyrated. However, the first end 610 of the mold 600 is also required to allow the foot portion 245 of the pressure ram 200 to enter the mold 600 to provide the compressive force on the sample 50. Accordingly, the securing device 720 further defines a bore 735 generally corresponding to the cylindrical portion 240 or ram shaft 225 of the ram head 230, wherein the bore 735 is configured to allow the cylindrical portion 240 or ram shaft 225 to move freely therethrough. The securing device 720 further defines a recess 740 extending from the inner end 725 and disposed in series with the bore 735. The recess 740 is configured to correspond to the foot portion 245 of the ram head 230 such that, when the ram head 230 is retracted from the mold 600, the foot portion 245 enters the recess 740 and lies flush with the inner end 725 so as to form a flat surface in connection with the inner end 725.

As previously discussed, the securing device 720 is configured to maintain the second end 630 of the mold 600 in sufficient contact with the bearing member 420 during the gyratory compaction process. Accordingly, the apparatus 10 may further include one or more biasing devices 900, such as, for example, a spring type device or other suitable device, operably engaged between the frame 100 and the securing device 720 for resiliently biasing the securing device 720 into engagement with the first end 610 of the mold 600, and thus urging the mold 600 against the bearing member 420. By maintaining the mold 600 in the proper position with respect to the bearing member 420, the gyration angle 640 can thus be better maintained during the gyratory compaction process. As implemented in embodiments of the present invention, for example, the frame 100 may include one or more mounts 180 adjacent to the pressure ram 200, whereby the one or biasing devices 900 are disposed between the one or more mounts 180 and the securing device 720. In some embodiments of the present invention, the fork 705 is engaged with the securing device 720, wherein both are biased toward the bearing member 420 by the one or more biasing devices 900. Accordingly, when the foot portion 245 of the pressure ram 200 is fully retracted, the securing device 720 and the fork 705 are drawn back against the one or more biasing devices 900 until the fork 705 is in the proper position to accept the mold 600 from the staging member 160 or for the mold 600 to be removed from the fork 705 onto the staging member 160. As such, when the mold 600 is inserted into the fork 705, the foot portion 245 can be moved into the first end 610 of the mold 600. The one or more biasing devices 900 then urge the securing device 720/fork 705 assembly toward the bearing member 420, whereby the moving fork 705 moves the mold 600 into engagement with the bearing member 420. Further movement of the foot portion 245, after the mold 600 is engaged with the bearing member 420, moves the fork 705 out of engagement with the flat portions 695a and the lip portions 695b of the flange 690a, while the one or more biasing devices 900 urges the securing member 720 into engagement with the first end 610 of the mold 600, whereafter the first end 610 of the mold 600 is supported by the securing device 720, but not the fork 705.

However, when the fork 705 is disengaged from the flat portions 695a, the mold 600 may be able to rotate during the gyratory compaction process, which is not always desirable. Accordingly, in the embodiment as shown in FIG. 6A, the securing device 720, which is typically constrained from rotational movement by the one or more biasing devices 900 or by other arrangements, may define, for example, a recess or receptacle 770 in the bearing surface 730 thereof. A position on the bearing surface 665 or the flange 690a of the mold 600 may correspondingly include a pin member 780 capable of extending into the receptacle 770 when the securing member 720 is engaged with the mold 600, whereby interaction of the pin member 780 and the receptacle 770 prevents the mold 600 from rotating, but still allows the bearing surfaces 665, 730 to interact so as to permit the mold 600 to pivot as necessary with respect to the securing member 720. One skilled in art will readily appreciate, however, that many different mechanisms may be implemented for preventing the mold 600 from rotating about the axis 150 when not supported by the fork 705 and the configuration described herein is not intended to be limiting in this respect. For example, the pin member 780 may be engaged with the securing device 720 while the receptacle is defined by the mold 600.

Further, since embodiments of the present invention, as previously described, include a gyration point 650 that moves according to the displacement of the pressure ram 200, the first end 610 of the mold 600 cannot be constrained from lateral movement if the required gyration angle 640 is to be achieved and maintained during the gyratory compaction process. Accordingly, as shown in FIG. 9A, the apparatus 10 may further include a lateral translation device 920 disposed between the securing member 720 and the one or more biasing devices 900 to thereby allow the securing device 720 to bias the mold 600 against the bearing member 420 while permitting the first end 610 of the mold 600 to freely laterally translate as needed. For example, the securing device 720 may be attached to a first translation plate 925 via one or more first sliding mechanisms 930 disposed therebetween, and the first translation plate 925 then attached to a second translation plate 935 via one or more second sliding mechanisms 940 disposed therebetween, wherein the second translation plate 935 is attached to the one or more biasing members 900. In some instances, the first sliding mechanism(s) 930 are disposed perpendicularly with respect to the second sliding mechanism(s) 940 to allow the securing member 720 to freely laterally translate with respect to the one or more biasing members 900. However, one skilled in the art will also appreciate that the free lateral translation of the securing member 720 may be accomplished in many different manners and that the configuration disclosed herein is not intended to be limiting in this respect.

Figure 10A:
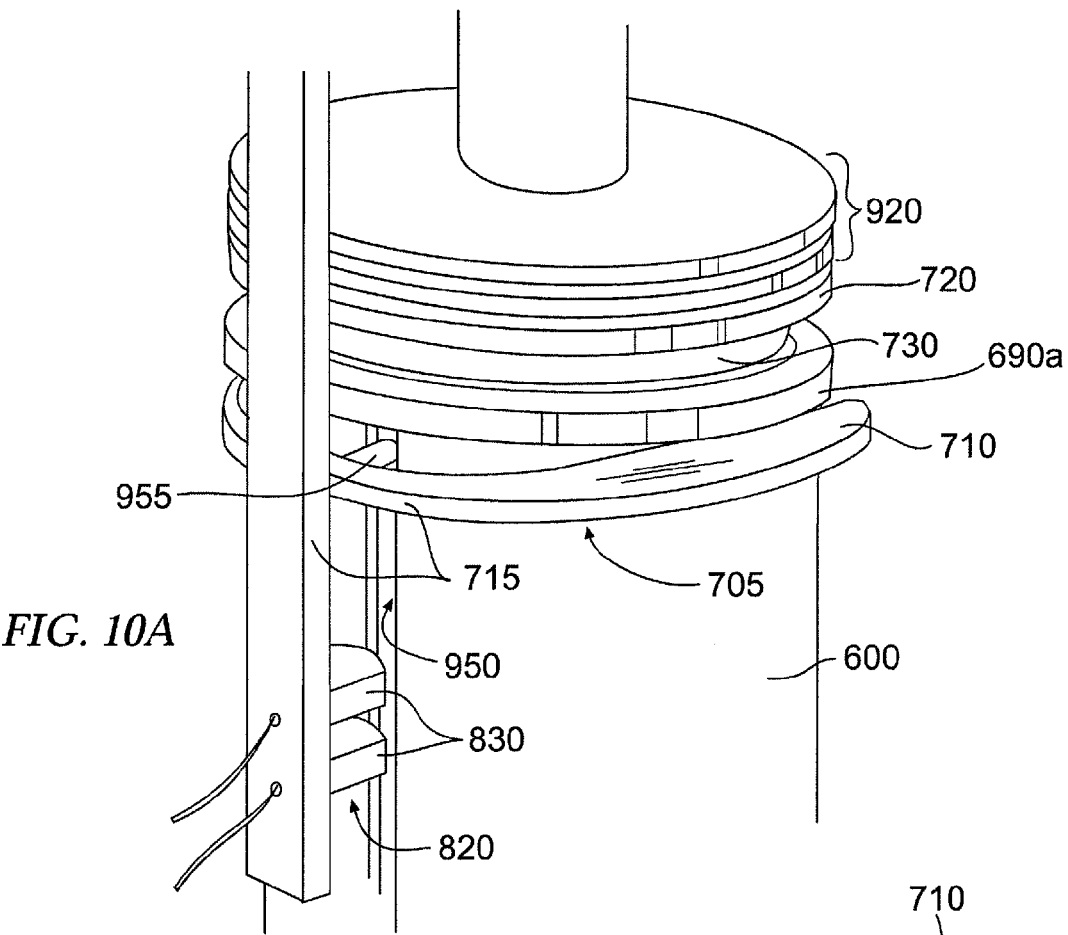
FIGS. 10A and 10B are schematics of a mold-handling device configured to manipulate a mold for a gyratory compactor apparatus according to another embodiment of the present invention.
Figure 10B:
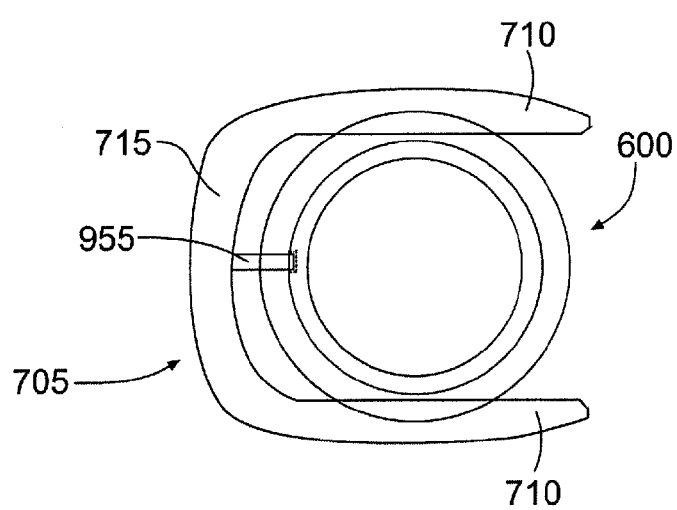

One skilled in the art will further appreciate that some components forming the apparatus 10 may be configured in different manners, or to cooperate with other components in different manners, to obtain the same or similar function and results as described herein. For example, in some embodiments of the present invention, as shown in FIGS. 10A and 10B, the fork 705 may be operably engaged with the pressure ram 200 instead of the securing device 720, or otherwise operated independently of both the pressure ram 200 and the securing device 720, such that the fork 705 moves independently of the securing device 720. In some instances, the fork 705 may be configured to move in correspondence with the foot portion 245 of the ram head 230. In such a configuration, the fork 705 may be disposed in the apparatus 10 to receive the mold 600 or to allow the mold 600 to be removed therefrom as previously described. However, for example, the flange 690a about the first end 610 of the mold 600 may be configured without the flat portions 695a, whereby the flange 690a itself supports the mold 600 when the mold 600 is received by the fork 705. In order to insure the proper rotational orientation of the mold 600 when inserted into the mold well 500, the mold 600 may, for instance, define an axially-extending groove 950 in the outer surface thereof, wherein the support member 715 or other component of the fork 705 may have a pin member 955 engaged therewith and extending therefrom so as to be capable of engaging the groove 950 when the mold 600 is received by the fork 705. In such instances, the pin member 955 is further configured with respect to the groove 950 so that proper engagement therebetween, to prevent the mold 600 from rotating about the axis 150, is maintained during the gyratory compaction process for a range of axial positions of the fork 705 along the mold 600 or for a range of gyration angles 640 of the mold 600. For example, the pin member 955 may be configured such that the axial position thereof in engagement with the groove 950 along the mold 600 corresponds to the axial position of the center point 210 of the foot portion 245 of the ram head 230 (the gyration point 650) within the mold 600 during the gyratory compaction process.

Still further, as shown in FIG. 10A, the mold angle sensing device 820 may also be incorporated into the support member 715 or other component of the fork 705 such that the sensors 830 are separated by a distance along and oriented parallel to the axis 150 and operate in a manner as previously described to determine the gyration angle 640. The sensors 830 may be contact or non-contacting type sensors or any other type of sensor suitable for accomplishing the described functions thereof. In some instances, the sensors 830 may be configured to determine when the mold 600 is within a specified proximity thereto before providing appropriate signals to the controller 810, the controller 810 subsequently allowing the apparatus 10 to be operated in response to the signals. In such instances, the mold angle sensing device 820 functions, for example, to indicate that the mold 600 is properly inserted and aligned in the mold well 500 or as a safety interlock for the apparatus 10.

FIGS. 11A-11D illustrate an alternate embodiment of a mold-handling device 700 for receiving and handling the mold 600 within the mold well 500. The mold-handling device 700, in this embodiment, includes a first mounting plate 1100 defining a hole 1110 through which the cylindrical portion 240 or ram shaft 225 of the pressure ram 200 extends. The first mounting plate 1100 is attached to the frame 100 so as to be disposed opposite the ram head 230 from the mold well 500. A second mounting plate 1200 also defines a hole 1210 through which the cylindrical portion 240 or ram shaft 225 of the pressure ram 200 extends, wherein the second mounting plate 1200 is disposed between the first mounting plate 1100 and the ram head 230. The second mounting plate 1200 is engaged with the first mounting plate 1100 by one or more biasing devices 1250 (wherein four such biasing devices 1250 are shown in this embodiment) configured to bias the second mounting plate 1200 away from the first mounting plate 1100.

A pair of pivoting members 1300 are pivotably engaged with the second mounting plate 1200, on either side of the hole 1210, wherein the pivoting members 1300 are configured to have parallel pivot axes 1310. Each pivoting member 1300 is disposed opposite the second mounting plate 1200 from the first mounting plate 1100 and is configured to have a medial pivot such that a portion of the pivoting member 1300 extends inwardly toward the hole 1250, while the opposing portion extends outwardly of the second mounting plate 1200. Each pivoting member 1300 further includes a pivot element 1350 engaged therewith and extending to the first mounting plate 1100 or the frame 100, with each pivot element 1350 being configured to pivot the respective pivoting member 1300 and/or limit the extent to which the respective pivoting member 1300 is capable of pivoting.

One skilled in the art will appreciate that, as described and shown, the second mounting plate 1200 is movable with respect to the frame 100/first mounting plate 1100, and the pivoting members 1300 are pivotable with respect to the second mounting plate 1200. Accordingly, as the second mounting plate 1200 is biased away from the first mounting plate 1100 by the biasing devices 1250, the second mounting plate 1200 and/or pivot elements 1350 restrain the pivoting members 1300 with respect to the first mounting plate 1100, thus causing the outwardly-extending portions of the pivoting members 1300 to pivot toward the first mounting plate 1100 about the pivot axes 1310. The pivot elements 1350 also serve to limit pivoting of the pivot members 1300 and movement of the second mounting plate 1200 away from the first mounting plate 1100. Further, since the cylindrical portion 240 or ram shaft 225 of the pressure ram 200 extends through both of the mounting plates 1100, 1200, the ram head 230 is capable of pivoting the pivoting members 1300 in the opposite direction. That is, when the ram head 230 is brought to the fully retracted position, away from the bearing member 420, the ram head 230 will bear on the inwardly-extending portion of the pivoting members 1300, thereby pivoting the pivoting members 1300 about the pivot axes 1310 in the reverse direction. At the same time, the ram head 230 moves the second mounting plate 1200 toward the first mounting plate 1100.

Figure 11A:
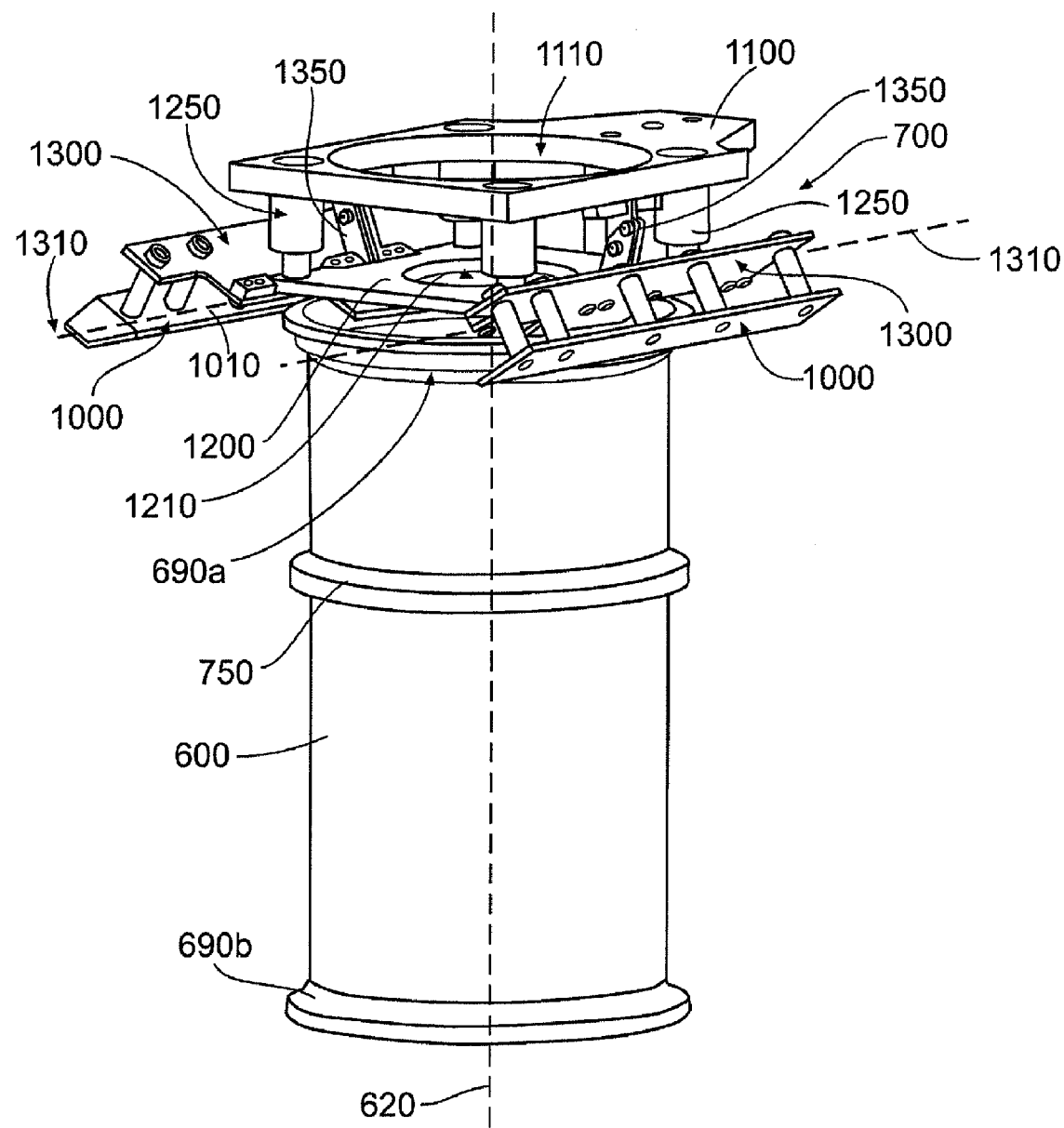
FIGS. 11A-11B are schematics of a mold-handling device configured to manipulate a mold for a gyratory compactor apparatus, the mold-handling device being in an open position, according to yet another embodiment of the present invention.
Figure 11B:
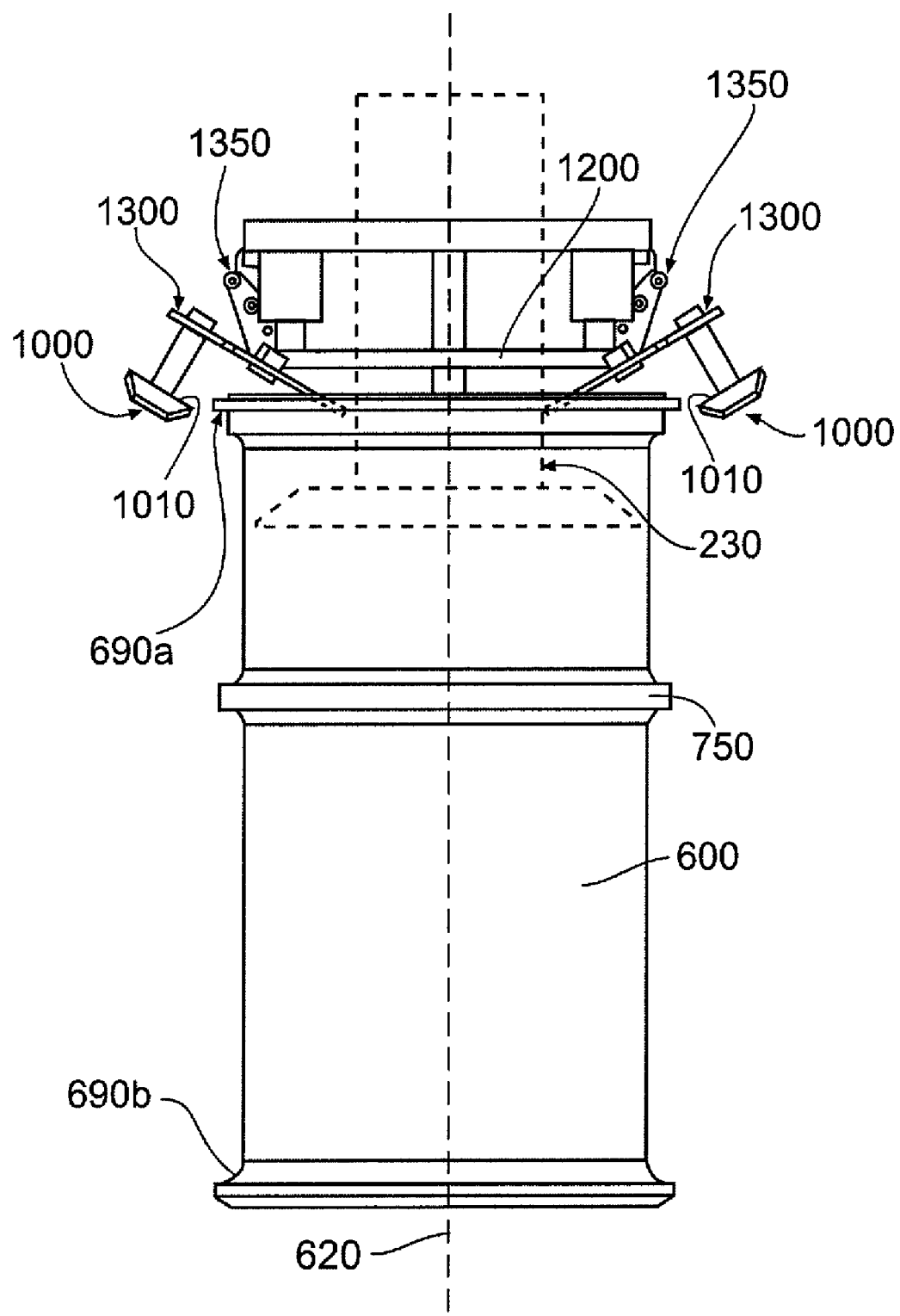

The pivoting elements 1300 each include a rail 1000 spaced apart therefrom, away from the second mounting plate 1200. Each rail 1000 includes an inwardly-extending support ledge 1010. When the ram head 230 is in the fully retracted position, the rails 1000 are sufficiently spaced apart so as to be capable of accepting the flange 690a at the first end 610 of the mold 600 therebetween, as shown in FIGS. 11A and 11B. The support ledges 1010 are spaced apart by more than the outer diameter of the mold 600, but less than the outer diameter of the flange 690a. When the ram head 230 is in the fully retracted position, the support ledges 1010 are at a sufficient height above the staging member 160 such that, when the mold 600 is urged into the mold well 500, the support ledges 1010 of the rails 1000 receive the mold 600 and support the mold 600, via the flange 690a, so that the second end 630 is above the level of the flat surface 430 of the bearing member 420. A mold stop (not shown) is engaged with the frame 100 and/or the mold-handling device 700 so as to stop the advance of the mold 600 into the mold well 500 from the staging member 160 when the longitudinal axis 620 of the mold 600 is aligned with the frame axis 150. Once the mold 600 is then inserted into the mold well 500 and supported by the rails 1000, the pressure ram 200 can be actuated to begin the compaction process.

Figure 11C:
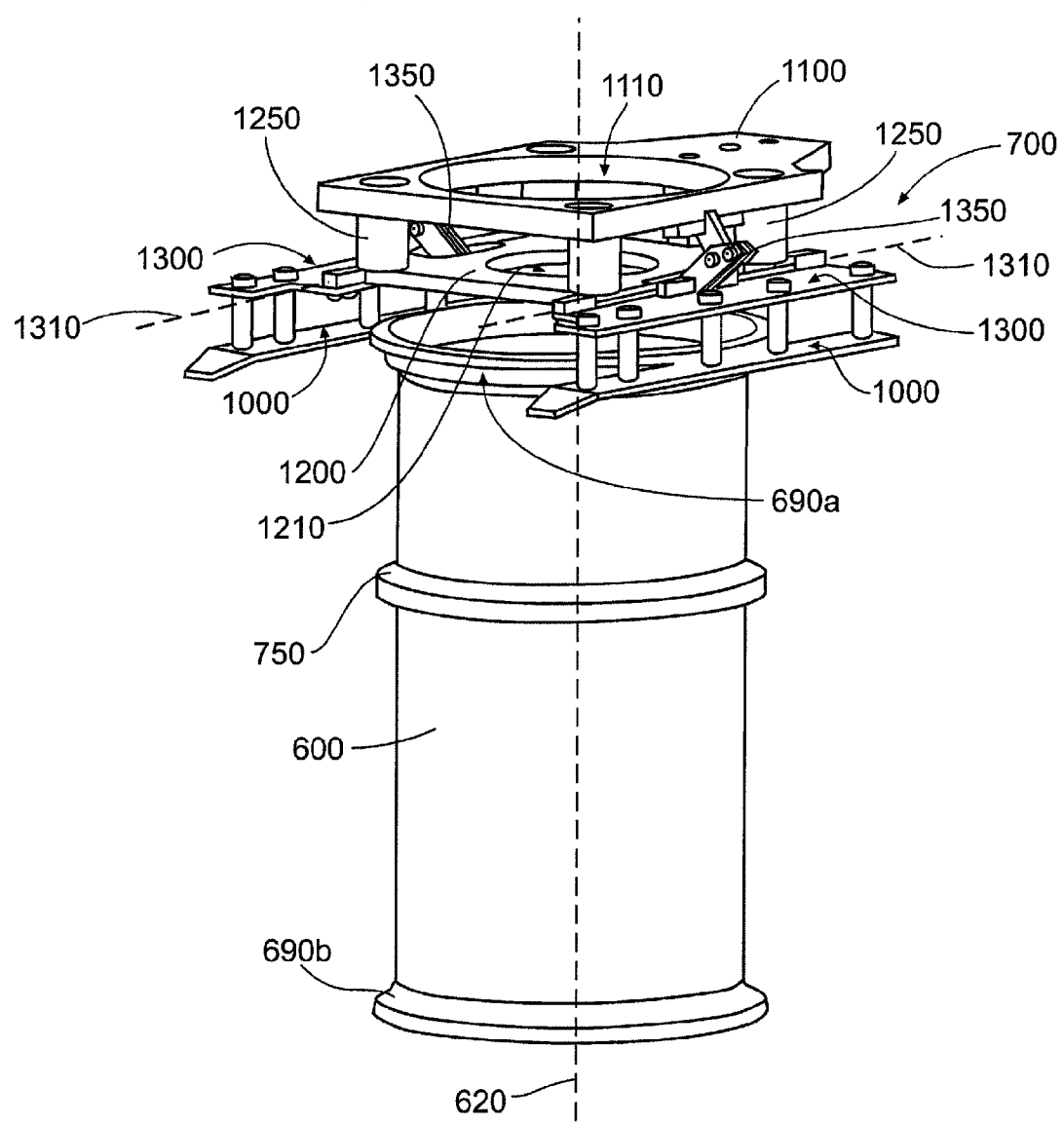
FIGS. 11C-11D are schematics of a mold-handling device configured to manipulate a mold for a gyratory compactor apparatus, the mold-handling device being in a closed position, according to the embodiment of the present invention shown in FIGS. 11A-11B.
Figure 11D:
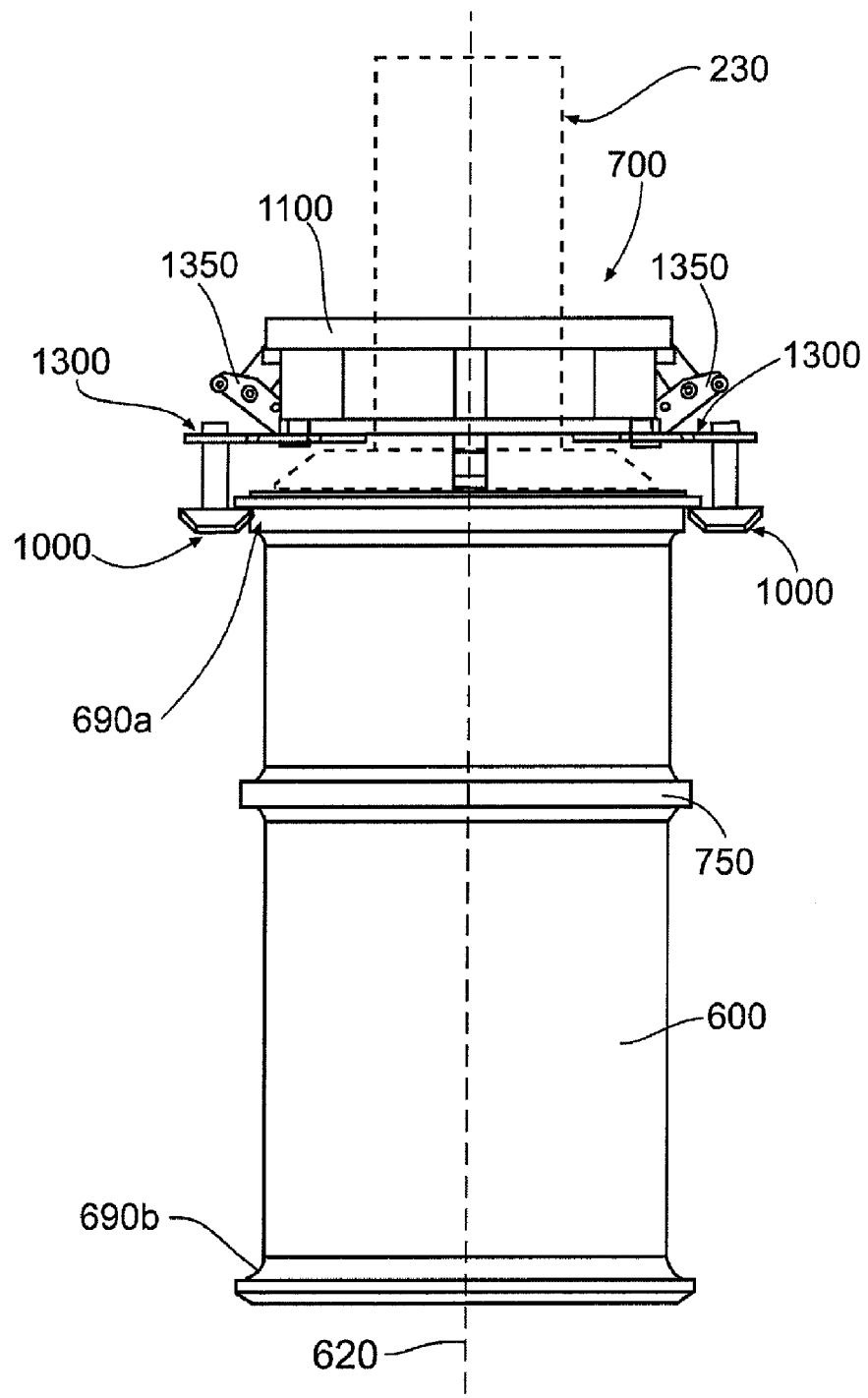

Upon actuation, the ram head 230 is directed into the first end 610 of the mold 600. As the ram head 230 moves into the mold 600, the biasing devices 1250 move the second mounting plate 1200 away from the first mounting plate 1100, thereby lowering the second end 630 of the mold 600 into engagement with the bearing member 420. Continued movement of the ram head 230 into the mold 600 allows the pivot elements 1350 to act upon the pivoting members 1300, thereby causing the pivoting members 1300, and thus the support ledges 1010 to pivot away from the flange 690a of the mold 600, as shown in FIGS. 11C and 11D. The mold-handling device 700 is further configured such that, when the support ledges 1010 pivot away from the flange 690a, the second end 630 of the mold 600 is already supported by the bearing member 420. Accordingly, certain embodiments of the present invention provide a substantially seamless transition between the mold 600 being lowered into engagement with the bearing member 420 and the mold-handling device 700 releasing the mold 600 as the pressure ram 200 begins the compaction process. At that point, further advancement of the pressure ram 200 causes the foot portion 245 in the mold 600 to provide the necessary axial compressive force on the sample 50 and establishment of the gyration angle 640.

Since the mold 600 is released by the mold-handling device 700 when the mold 600 is engaged with the bearing member 420 and the pressure ram 200 is beginning the compaction process, the mold 600 must be held in position with respect to the bearing member 420 so as to be substantially prevented from rotating about the longitudinal axis 620. Accordingly, in some embodiments using a mold-handling device 700 as discussed in connection with FIGS. 11A-11D, and as shown in FIG. 13, the mold 600 includes a medial flange 750 disposed between the first and second ends 610, 630. The medial flange 750 further defines a gap 755 extending circumferentially along the outer surface of the mold 600. An anti-rotation member 760 is engaged or otherwise in communication with the frame 100 and is configured to interact with the gap 755 in the medial flange 750. The anti-rotation member 760, in one embodiment, is disposed in the mold well 500 and normally biased outwardly of the mold well 500 toward the staging member 160 by a biasing device 765. When the mold 600 is inserted into the mold well 500 from the staging member 160, the anti-rotation member 760 engages the medial flange 750, and the mold 600 is rotated until the anti-rotation member 760 engages the gap 755. At the same time, the mold 600 is being received by the mold-handling device 700 and, as such, the anti-rotation member 760 may also serve to provide proper alignment of the mold 600 within the mold-handling device 700 and/or as the mold stop for indicating that the mold 600 is properly inserted into the mold-handling device 700 such that the longitudinal axis 620 is aligned with the frame axis 150. Accordingly, once the mold 600 is received by the mold-handling device 700 and supported by the rails 1000, the biasing device 765 maintains the anti-rotation member 760 in engagement with the gap 755 so as to substantially prevent the mold 600 from rotating during the compaction process.

Figure 12A:
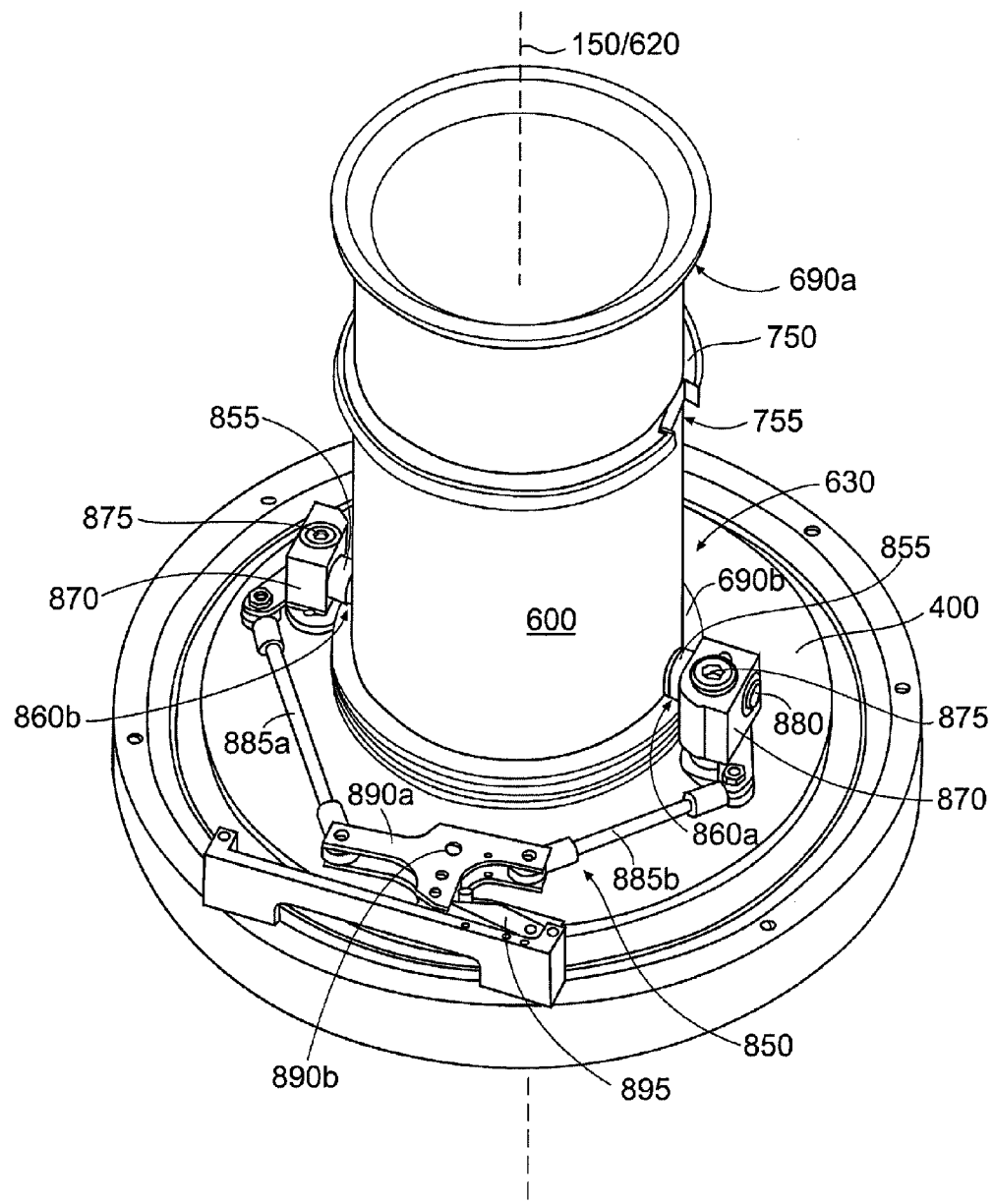
FIGS. 12A and 12B are schematics of a mold-securing mechanism configured to interact with a mold for a gyratory compactor apparatus according to one embodiment of the present invention.
Figure 12B:
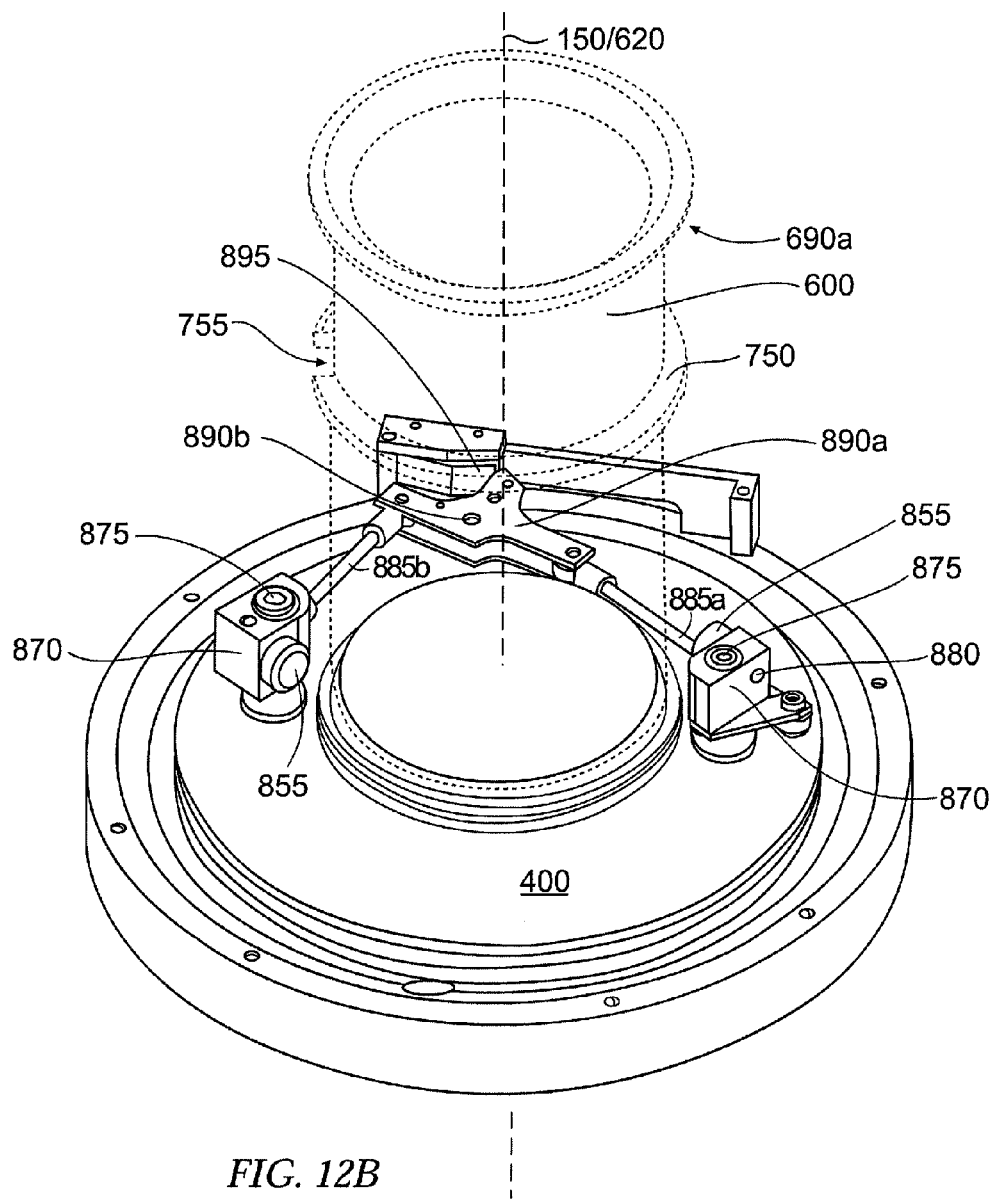

In holding the mold 600 in position with respect to the bearing member 420, consideration must also be given to preventing the mold 600 from lifting off the bearing member 420. That is, the mold 600 must be held down or otherwise maintained in proper contact with the bearing member 420 during the compaction process. Accordingly, in some embodiments using a mold-handling device 700 as discussed in connection with FIGS. 11A-11D, and as shown in FIGS. 12A and 12B, some embodiments of the present invention may further include a hold-down device 850 for securing the mold 600 to the bearing member 420 at the second end 630. By the hold-down device 850 maintaining the mold 600 in the proper position with respect to the bearing member 420, the gyration angle 640 can be better maintained during the gyratory compaction process. As the mold 600 is gyrated during the compaction process, the second end 630 of the mold 600 orbits around the frame axis 150. Accordingly, at any position in the orbit, the flange 690b at the second end 630 of the mold 600 will have two diametrically-opposed locations 860a, 860b at the same vertical level with respect to the bearing member 420. That is, at any instant during the orbit, a plane aligned along the longitudinal axis 620 of the mold 600 and extending tangentially to the gyration center 410 of the bearing member 420 will intersect the flange 690b at the second end 630 of the mold 600 at two points. The intersection points of the plane with the flange 690b thus define the same longitudinal locations 860a, 860b diametrically-opposed about the flange 690b. However, one skilled in the art will appreciate that, since the mold 600 is substantially prevented from rotating about the longitudinal axis 620 as the mold 600 is gyrated, the same longitudinal locations 860a, 860b move around the flange 690b in the same rotational direction imparted to the offsetable member 400 as it orbits around the frame axis 150.

As such, in one embodiment, the hold-down device 850 comprises a pair of roller members 855 mounted so as to be diametrically opposed with respect to the bearing member 420. The roller members 855 are mounted to respective mounting blocks 870, with each mounting block 870 being rotatable about a respective longitudinally-extending pin member 875 engaged with the offsetable member 400. The roller members 855 are mounted to the respective mounting block 870 via a laterally-extending axle 880. The mounting blocks 870 are thus configured to be pivotable so that the roller members 855 can be moved from a first position, as shown in FIG. 12A, in which the roller members 855 are disposed over the flange 690b to a second position, as shown in FIG. 12B, in which the roller members 855 and the mounting blocks 870 are disposed radially outward of the flange 690b. In the first position, the axles 880 are disposed along a line extending through the gyration center 410 such that the roller members 855 are oriented tangentially to the outer surface of the mold 600. In the second position, the mounting blocks 870 and the rollers members 855 are disposed such that the mold 600 can be lifted from the bearing member 420 without interference.

The mounting blocks 870 are connected by respective arms 885a, 885b to a position-controlling member 890a mounted so as to be rotatable about a longitudinally-extending pin member 890b engaged with the offsetable member 400. In one embodiment, the position-controlling member 890a and/or the mounting blocks 870 may be biased to a normal rotational position such as, for example, where the roller members 855 are disposed so as to engage the flange 690b, or where the roller members 855 are disposed radially outward of the flange 690b. In some instances, the position-controlling member 890a and/or the mounting blocks 870 may be biased to both opposing normal positions, wherein the transition between those positions are determined by a cam or other mechanism or device for allowing such biasing on either side of a transition point. The arms 885a, 885b are engaged between the position-controlling member 890a and the respective mounting blocks 870 such that, as the position-controlling member 890a is rotated in one direction, the roller members 855 are moved into engagement with the flange 690b, while the roller members 855 are moved away from the flange 690b when the position-controlling member 890a is rotated in the opposite direction.

One skilled in the art will appreciate that, before the compaction process can begin, the mold 600 must be moved into engagement with the bearing member 420 and secured thereto by the roller members 855. At the same time, the mold 600 is prevented from rotating about the longitudinal axis 620 by the anti-rotation member 760. The position-controlling member 890a and the mounting blocks 870 are secured to the offsetable member 400, which does not rotate about the gyratory center 410. Accordingly, as the mold 600 is gyrated, the position-controlling member 890a and the mounting blocks 870 move in the orbit with the offsetable member 400, and the roller members 855 thereby roll around the flange 690b of the mold 600, in correspondence with the same vertical level locations 860a, 860b, while securing the mold 600 to the bearing member 420.

In some instances, the apparatus 10 may also include a ratcheting member 895 engaged with the frame 100 and capable of engaging the position-controlling member 890a. That is, the ratcheting member 895 may be mounted such that, as the offsetable member 400 is moved in the orbit by the rotatable member 300 in a normal rotation direction, the ratcheting member 895 initially contacts the position-controlling member 890a and rotates the position-controlling member 890a into the position in which the roller members 855 engage the flange 690b to secure the mold 600 to the bearing member 420. The ratcheting member 895 may be resiliently biased toward a contact position with the position-controlling member 890a, or may otherwise be selectively actuatable to the contact position. Upon completion of the compaction process, the roller members 855 must be disengaged from the flange 690b in order for the mold 600 to be removed from the apparatus 10. As such, in one embodiment, the rotatable member 300 may be capable of being directed in reverse with respect to the normal rotation direction. In such an instance, the ratcheting member 895 may be configured to contact the position-controlling member 890a and cause the position-controlling member 890a to rotate into the position in which the roller members 855 are disengaged from the flange 690b, thereby allowing the mold 600 to be removed by retraction of the pressure ram 200.

In certain embodiments of the present invention, the position-controlling member 890a and/or the mounting blocks 870 may be engaged with a limit switch (not shown) or another type of detection mechanism to determine when the position-controlling member 890a has been rotated into the position in which the roller members 855 are disengaged from the flange 690b and to stop the reverse rotation of the rotatable member 300 in response thereto. In some instances, the limit switch or other detection mechanism may also direct or actuate the offsetable member 400 to return to a home position such that the longitudinal axis 620 of the mold 600 realigns with the frame axis 150. Accordingly, the state in which rotation of the rotatable member 300 has ceased, the roller members 855 are disengaged from the flange 690b, and the offsetable member 400 has returned to the home position may be defined as a register state. In the register state, the pressure ram 200 may be actuated to retract from the mold 600, thereby causing the mold-handling device 700 to begin the process of lifting the mold 600 from the bearing member 420 so as to allow the mold 600 to be removed from the mold well 500.

FIGS. 14A and 14B show one embodiment of a mold angle sensing device 820, wherein the sensors 830 are configured as contacting type sensors. Such a configuration of a mold angle sensing device 820 may be used in conjunction with any embodiments of the present invention, but is described herein with embodiments using a mold-handling device 700 as discussed in connection with FIGS. 11A-11D. The sensors 830 are normally biased toward the mold 600 by, for example, springs (not shown). In some instances, such as, for example, to perform apparatus testing calibration procedures, or the like, the pressure ram 200 may need to be lowered toward the bearing member 420 without the mold 600 in place within the mold well 500. In those instances, the sensors 830 protruding into the mold well 500 may be at risk of damage due to contact with the ram head 230. Accordingly, the mold angle sensing device 820 may also include a sensor guard 840 capable of moving and retaining the sensors 830 out of the path of the ram head 230. As shown, the sensor guard 840 may be pivotably attached to the mold angle sensing device 820 and having a free end 845 movable between an inoperative position, away from the sensors 830, as shown in FIG. 14A, and an operative position, as shown in FIG. 14B, where the free end 845 engages the sensors 830 so as to recess the sensors 830 into the mold angle sensing device 820. In the operative position, the free end 845 may be secured to the mold angle sensing device 820 so as to retain the sensors 830 out of the path of the ram head 230.

Many modifications and other embodiments of the invention set forth herein will come to mind to one skilled in the art to which this invention pertain having the benefit of the teachings presented in the foregoing descriptions and the associated drawings. For example, the apparatus 10 may be configured to receive and manipulate the mold 600 in various orientations, such as "upside down" or horizontally, subject to the aforementioned requirements of the gyratory compaction process. More particularly, for instance, the apparatus 10 may be configured and oriented such that the pressure ram 200 exerts the necessary pressure from a lower end of the mold 600. Accordingly, in such instances, the offsetable member 400/rotatable member 300 assembly would be disposed toward the upper end of the mold 600 and, as such, one skilled in the art will appreciate that an appropriate securing device (not shown) for securing the mold 600 to the offsetable member 400 will be required along with an appropriate mold-handling device 700. Other components of the apparatus 10 will also need to be appropriately configured. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A device adapted to determine and maintain an angle of gyration of a mold engaged with a gyratory compactor apparatus defining an axis, the mold being generally cylindrical, defining an axis, and having opposed first and second ends, the mold being gyratable about the apparatus axis at a gyration point displaced from the second end toward the first end, said device comprising:
- an offsetable member adapted to be capable of engaging the second end of the mold in displacement from the apparatus axis and to be movable in an orbital motion about the apparatus axis so as to cause the mold to gyrate with respect to the gyration point, the gyration point being remotely disposed with respect to the second end of the mold;
- a sensor device configured to dynamically determine an actual angle of gyration of the mold, the actual angle of gyration being related to the displacement of the offsetable member, the gyration point, and the apparatus axis; and
- a controller operably engaged with the offsetable member so as to be capable of directing adjustment of the displacement of the offsetable member to provide a desired angle of gyration with respect to the gyration point, the controller being in communication with the sensor device and responsive thereto so as to be capable of dynamically adjusting the displacement of the offsetable member to maintain the actual angle of gyration substantially equal to the desired angle of gyration.

2. A device according to claim 1 further comprising a rotatable member configured to be rotatable about the apparatus axis, the rotatable member being configured to support the offsetable member such that the offsetable member is laterally movable with respect thereto.

* * * * *